(12) United States Patent
Moskal et al.

(10) Patent No.: US 6,566,060 B1
(45) Date of Patent: May 20, 2003

(54) METHODS FOR DETECTION AND TREATMENT OF DISEASE USING A GLYCOSYLTRANSFERASE

(75) Inventors: Joseph R. Moskal, Chicago, IL (US); Hirotaka Yamamoto, Glenview, IL (US)

(73) Assignee: Chicago Institute of Neurosurgery and Neuroresearch, Chicago, IL (US)

( * ) Notice: Subject to any disclaimer, the term of this patent is extended or adjusted under 35 U.S.C. 154(b) by 0 days.

(21) Appl. No.: 09/450,195

(22) Filed: Nov. 29, 1999

Related U.S. Application Data

(62) Division of application No. 08/969,437, filed on Nov. 12, 1997, now abandoned.

(51) Int. Cl.$^7$ .......................... C12Q 1/48; C07H 21/02; C07H 21/04; C07K 14/00
(52) U.S. Cl. .................. 435/6; 536/23.1; 536/24.3; 530/350
(58) Field of Search ............... 435/4, 6; 530/350; 536/23.1, 24.3; 935/76, 77, 78

(56) References Cited

U.S. PATENT DOCUMENTS

| | | | | |
|---|---|---|---|---|
| 5,605,807 A | * | 2/1997 | Dennis | 435/15 |
| 5,856,159 A | | 1/1999 | Perez | 435/193 |
| 5,858,751 A | | 1/1999 | Paulson et al. | 435/193 |
| 5,874,261 A | | 2/1999 | Roth | 435/97 |
| 5,874,271 A | | 2/1999 | Nishikawa et al. | 435/193 |
| 5,955,282 A | | 9/1999 | Hillman et al. | 435/6 |
| 5,955,347 A | | 9/1999 | Lowe | 435/252.3 |
| 5,962,294 A | | 10/1999 | Paulson et al. | 435/193 |
| 6,015,701 A | | 1/2000 | Pierce et al. | 435/193 |

OTHER PUBLICATIONS

Ito et al., International J. of Cancer 71 : 556–564 (1997).*
Yamamoto et al., Glycocongugate Journal 12: 848–856 (1995).*
Lotan, et al., (1984), *Cancer Res.*, 44:5805–5812.
Bresalier, et al., (1990), *Cancer Res.*, 50:1299.
Shah, et al., (1992), *J. Biol. Chem.*, 267:10652–10658.
Sata, et al., (1991), *Am. J. Pathol.*, 139:1435–1448.
Marer, et al., (1992), *Glycobiology*, 2:49–56.
Kaneko, et al., (1996), *Acta Neuropathol*, 91:284–292.
Collard, et al., (1986), *Cancer Research*, 46:3521–3527.
Livingstone, et al., (1988), *J. Biol. Chem.*, 263:9443–9448.
Kojima, et al., (1994), *J. Bio. Chem.*, 269:30451–30456.
Nakagawa, et al., (1985), *Br. J. Cancer*, 51:357–363.
Toribara, et al., (1989), *Cancer Res.*, 49:3321–3327.
Werkmeister, et al., (1983), *Int. Cancer*, 32:71–78.
Passaniti, et al., (1988), *J. Biol. Chem.*, 263:7591–7603.
Gornati, et al, (1995), *Cancer Biochem. Biophys.*, 15:1–10.
Grimes, W.J., (1973), *Biochemistry*, 12:990–996.
Schirmacher, et al., (1982), *Invasion Metastasis*, 2:313–360.

* cited by examiner

*Primary Examiner*—Ethan C. Whisenant
(74) *Attorney, Agent, or Firm*—McDonnell Boehnen Hulbert & Berghoff

(57) ABSTRACT

The present invention relates to the prevention and treatment of a disease, preferably brain cancer, by administration of an isolated DNA molecule comprising a gene encoding a protein having glycosyltransferase activity to a cell involved in the disease which is preferably a glioblastoma cell. A method of treating brain cancer is provided in which a tumor cell is transfected either ex vivo or in vivo with a composition comprising a DNA molecule that encodes a protein having glycosyltransferase activity resulting in inhibition of the growth or function of that cell.

3 Claims, 20 Drawing Sheets

| Transcriptional Regulatory Region | Nucleic Acid Encoding Glycosyltransferase |
|---|---|
| Examples of Transcriptional Regulatory Regions | Nucleic Acid Encoding Glycosyltransferase |
| CMV immediate-early enhancer/promoter | α2,6-ST |
| SV40 early enhancer/promoter | α2,3-ST |
| JC polyomavirus promoter | SLex-ST |
| Chicken β-actin promoter coupled to the CMV enhancer | Fuco |
| | HexB |
| | GnTI |
| | GnTIII |
| | GnTV |

FIGURE 3

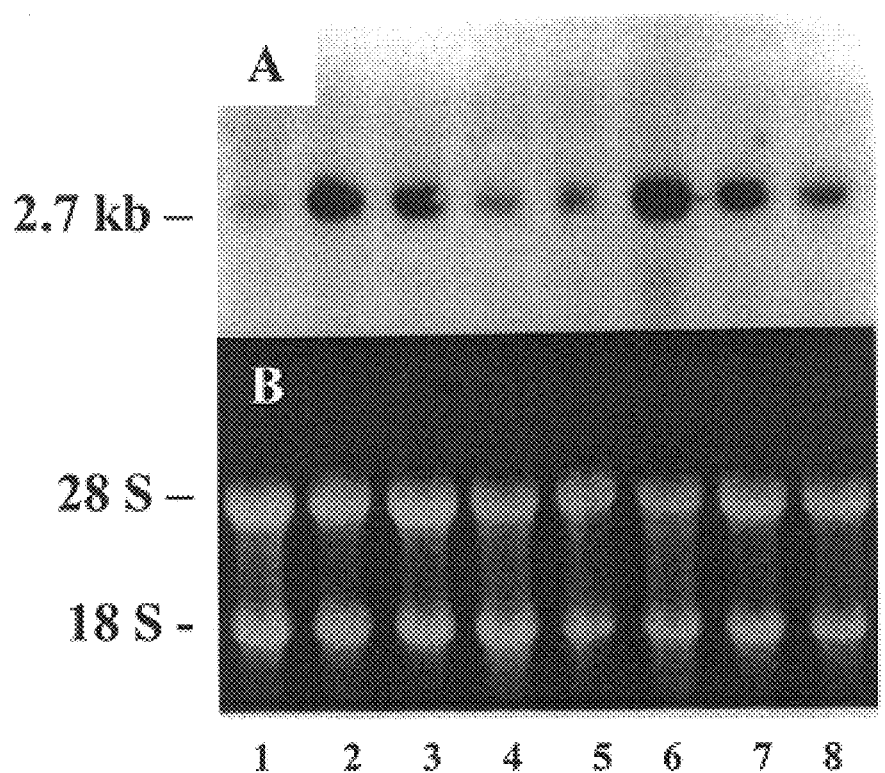
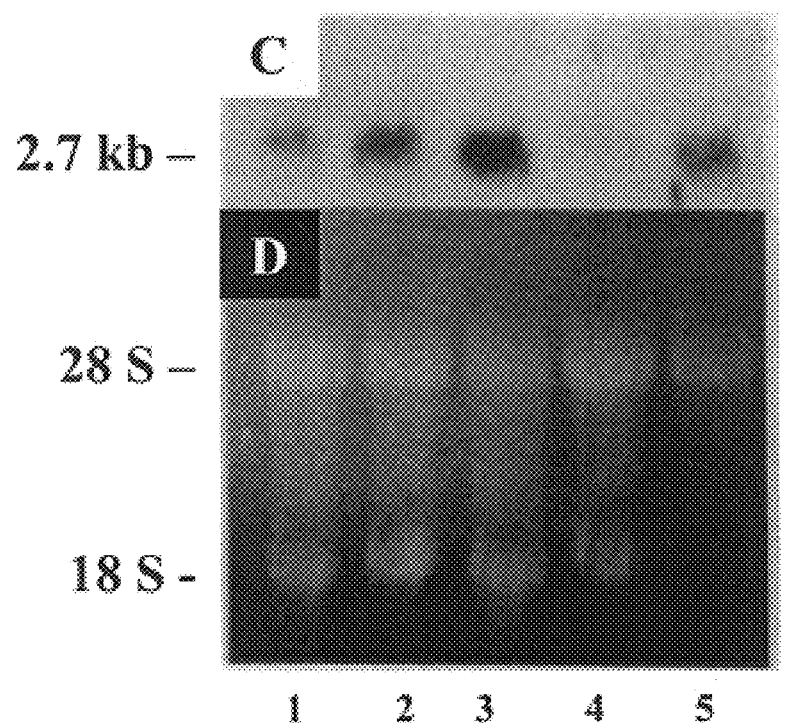
FIGURE 5

Plasmid name: pCMVgeneral vector
Plasmid size: 4.30 kb
Constructed by: Swaminathan
Construction date: June 1993
Comments/References: Starting plasmid was pCMVE4 6/7. The E4 6/7 seqs. were removed by cutting with Hind III (@1.97) and Eco RI (@1.24) and replaced with an oligo carrying Hind III, Bgl II and Xho I. The original Hind III & Eco RI sites are destroyed in this construct.

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence

```
<220> FEATURE:
<223> OTHER INFORMATION: alpha 2,3-ST sense primer

<400> SEQUENCE: 1
ctggactcta aactgcctgc                                              20

<210> SEQ ID NO 2
<211> LENGTH: 17
<212> TYPE: DNA
<213> ORGANISM: Artificial Sequence
<220> FEATURE:
<223> OTHER INFORMATION: alpha 2,3-ST antisense primer

<400> SEQUENCE: 2
cccagagact tgttggc                                                 17

<210> SEQ ID NO 3
<211> LENGTH: 22
<212> TYPE: DNA
<213> ORGANISM: Artificial Sequence
<220> FEATURE:
<223> OTHER INFORMATION: FAK sense primer

<400> SEQUENCE: 3
atggcagctg cttaccttga cc                                           22

<210> SEQ ID NO 4
<211> LENGTH: 21
<212> TYPE: DNA
<213> ORGANISM: Artificial Sequence
<220> FEATURE:
<223> OTHER INFORMATION: FAK antisense primer

<400> SEQUENCE: 4
ttcatatttc cactcctctg g                                            21
```

METHODS FOR DETECTION AND TREATMENT OF DISEASE USING A GLYCOSYLTRANSFERASE

This application is a division of U.S. application Ser. No. 08/969,437 filed Nov. 12, 1997, now abandoned.

FIELD OF THE INVENTION

The present invention relates to the prevention and treatment of disease by administration of an isolated DNA molecule comprising a gene encoding a protein having glycosyltransferase activity to a cell. In one embodiment of the present invention, a method of treating brain cancer is provided in which a tumor cell is transfected with a DNA molecule that encodes a protein having glycosyltransferase activity resulting in inhibition of the growth or function of that cell.

BACKGROUND OF THE INVENTION

Cell surface glycoproteins and glycosphingolipids appear to play an important role in a diverse array of cellular functions including regulation of cell growth, differentiation and intercellular communication (Moskal, 1987; Hakomori, 1981). Glycosylation is known to play various roles in host cell-viral interactions, immune cell recognition and migration, neural cell adhesion and function and the function of gonadotropic hormones (Rademacher, 1988). A defect in the glycosyltransferase function has been associated with several inherited diseases. Congenital dyserythropoietic disease, a condition in which abnormal morphologies are detected in various immune cells is observed, has been attributed to a deficiency of GlcNAc transferase II (Fukuda, et al. 1987. *J. Biol. Chem.* 262:7195–7206). I-cell disease and pseudo-Hurler polydystrophy, involving a deficiency of phospho-N-acetylglucosamninyl transferase activity, are also genetic diseases involving defective oligosaccharide biosynthesis (Kornfeld, 1986. Clin. Invest. 77:1–6).

Alterations in the expression of terminal sialic acid residues on glycoconjugates are common phenomena in oncogenic transformation (Kaneko, 1996; Nicholson, 1982; Roth, 1993; Schirrmacher, 1982; Varki, 1993). Increased cell-surface sialylation has been implicated in invasivity (Collard, 1987), tumor cell-mediated platelet aggregation (Bastida, 1987), resistance to T-cell mediated cell death (Workmeister, 1983), adhesion to endothelial cells and extracellular matrices (Dennis, 1982), and metastatic potential (Passanti, 1988). Studies have shown a correlation between increased terminal sialylation of cell-surface glycoproteins and both the metastatic and invasive potential of a variety of tumors (Collard, 1987; Nicholson, 1982; Passanti, 1988, Varki, 1993). It has also been reported that terminal sialylation of glycoproteins found in human chronic myelogenous leukemia K562 cells increases their resistance to T-cell-mediated cell lysis (Workmeister, 1987).

At least ten distinct enzymes are known to transfer sialic acid to the termini of the oligosaccharide moieties of glycosphingolipids and glycoproteins, termed sialyltransferases. These enzymes comprise a structurally related family of molecules that display substrate specificity, tissue specificity, and are developmentally regulated (Kitagawa, 1994). There are at least two sialyltransferases which transfer sialic acid to the nonreducing termini of sugar chains of N-linked glycoproteins. One is CMP-NeuAc:Galβ1,3(4)GlcNAc α2,3-sialyltransferase (α2,6-ST); another is CMP-NeuAc:Galβ1,3(4)GlcNAc α2,3-sialyltransferase (α2,3-ST). These transferases have been shown to be cell-type specific and appear to modulate a variety of important cellular processes. It is currently appreciated by those skilled in the art that alterations in the glycosylation of cell surface molecules involved in invasivity (e.g., gangliosides, growth factor receptors, etc.) may have a distinct effect on the tumorigenic and metastatic potential of tumor cells.

Applicants believed their system would be most stringently tested using a disease model having a high incidence of mortality and a low number of treatment options. Brain cancer represents an extremely aggressive form of cancer which is generally associated with a poor prognosis. Presently, treatment of brain cancer is limited in its efficacy and there is a need in the field for efficient and successful strategies for treating brain cancer. While a number of investigators have used cell lines derived from vertebrate brain tumors to study the expression and regulation of various glycosyltransferase (Demetriou, 1995; Takano, 1994; La Marer, 1992), studies using primary human brain tumor material have been very limited. Shen et al. (1984) reported that serum sialyltransferase, using desialylated fetuin as the acceptor, did not significantly differ from controls in glioma patients. Gornati et al. (1985) found that the sialyltransferase involved in the biosynthesis of GD3 from GM3 ganglioside was altered in meningiomas.

The present application provides a methodology that, in at least one embodiment, involves transfer of a gene encoding a protein having glycosyltransferase activity to a cell derived from a primary tumor or a cell line. Applicants herein provide a methodology provide a method with which a neurological disorder such as brain cancer may be treated by altering expression of a protein having sialyltransferase activity, preferably α2,6-ST and/or α2,3-ST, within a cell. It is recognized by those skilled in the art that there is a need for methodologies with which to treat such disorders, as there is a lack of effective treatments resulting in the suffering and eventual death of many victims of such diseases. The invention of this application provides reagents and methodologies for treatment of a neurological disorder such as brain cancer.

BRIEF DESCRIPTION OF THE FIGURES

FIG. 3. Glycosyltransferase and Sialyltransferase Nucleic Acid Constructs.

FIG. 5. Expression of α2,3-ST in human brain tumor cell lines and fetal astrocytes. All lanes were loaded with 20 µg total RNA. Panel 5A. Lanes 1–5: human glioma cell lines SNB-19, SW1088, U-1118MG, U-373MG, and U87MG, respectively; lanes 6–8: human neuroblastoma cell lines SKN-MC, LAN-S, and IMR 32, respectively. All brain tumor cell lines expressed α2,3-ST mRNA. Ethidium bromide staining of total RNA is shown in panel 5B. Panel 5C. Lane 1: human neuroblastoma IMR 32; lane 2: human neuroblastoma LAN-S; lane 3: cultured human fetal astrocytes; lane 4: human glioma U-373MG; lane 5: human glioma U-118MG. Ethidium bromide staining of total RNA is shown in panel 5D.

SUMMARY OF THE INVENTION

An objective of the present invention is to provide reagents and methodologies that meets a need in the art for a treatment for a disease condition. As an example of such a disease condition, Applicants have demonstrated the reagents and methodologies of the present invention using a neurological disease model. Many neurological disorders such as brain cancer, Parkinson's disease and Alzheimer's disease are associated with a poor prognosis. Options for treatment of these diseases is currently extremely limited. The present invention provides a reagents and methodologies with which such a prognosis may be improved. It is to be understood that the Applicants' invention may also prove useful in the treatment and prevention of a disease in which alterations in the glycosylation of certain proteins is involved.

In one embodiment of the present invention, a method of treating a neurological disorder comprising transfection of an isolated nucleic acid molecule encoding a protein having glycosyltransferase activity into a target cell. Preferably, expression of the protein having glycosyltransferase activity within the target cell preferably decreases the ability of that cell to proliferate or function or increases the ability of the host immune system to recognize the target cell. More preferably, and due to any of multiple possible mechanisms, the target cell is unable to survive following expression of the protein Preferably, the glycosyltransferase is α2,6-ST, α2,3-ST, SLex-ST, Fuco, HexB, GnTI, GnTIII, and GnTV.

In another embodiment of the present invention, a viral vector comprising a nucleic acid encoding a glycosyltransferase protein is provided. In another embodiment, a method for treating a neurological disorder using a viral vector such as that described above is provided. Preferably, the glycosyltransferase is α2,6-ST, α2,3-ST, SLex-ST, Fuco, HexB, GnTI, GnTIII, and GnTV.

DETAILED DESCRIPTION

Within this application, unless otherwise stated, the techniques utilized may be found in any of several well-known references including: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), and *Gene Transfer and Expression Protocols*, pp. 109–128, ed. E. J. Murray, The Humana Press Inc., Clifton, N.J.).

Figure 1:
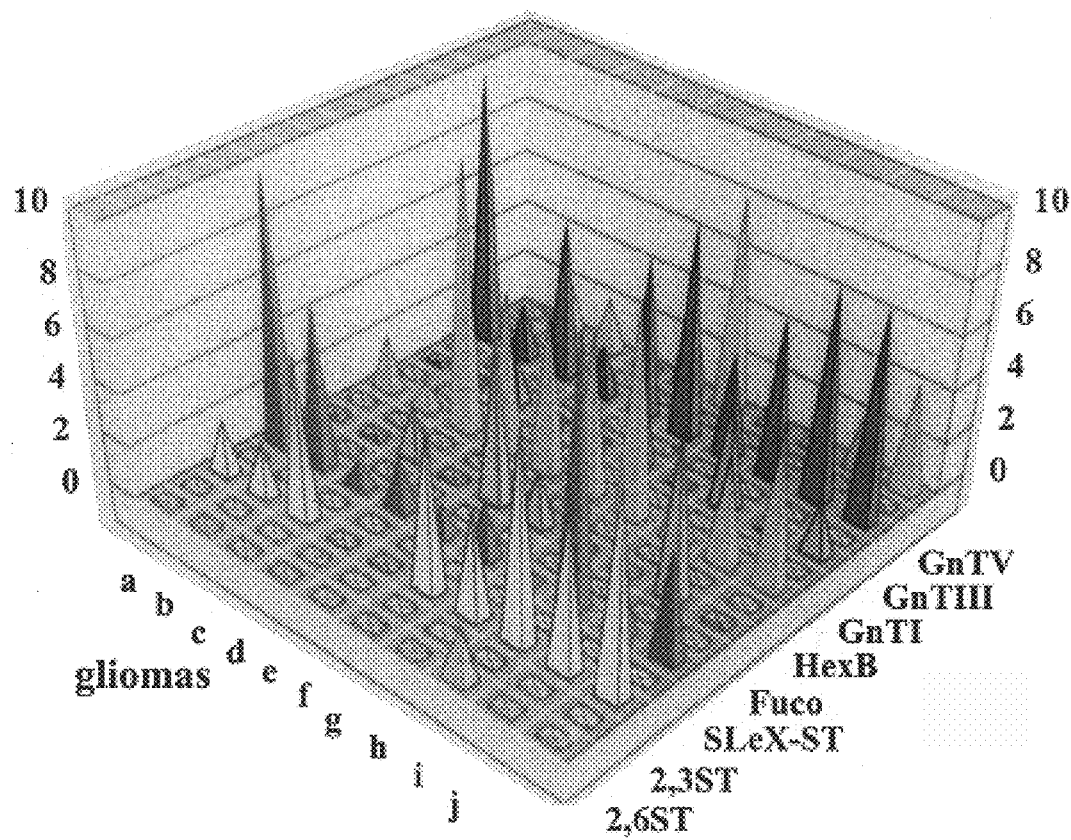
FIG. 1. Glyco-Enzyme mRNA Expression in Gilomas.

The types and amounts of glycosyltansferase enzymes found within neural tissues varies signficantly. Applicants have previously reported that α2,6-ST is expressed in a wide variety of normal human and rat tissues, including the skin, hematopoietic tissues, esophagus, liver, kidney, uterus and placenta (Kaneko, 1995). In addition, that study demonstrated α2,6-ST expression in normal choroid plexus epithelial and ependymal cells of the nervous system (Kaneko, 1995). α2,3-ST has been shown to be expressed primarily in skeletal muscle, brain and most fetal tissues (Kitagawa, 1994). The variation of mRNA expression of glycosyltransferase enzymes is demonstrated in FIGS. 1 and 2. As indicated in FIG. 1, the majority of gliomas tested express low levels of α2,6-ST, Fuco, GnTI and GnTV but express higher levels of α2,3-ST, SLex-ST, HexB, and GnTIII. In order to alter the patterns of glycosylation or sailylation on such cells, the levels of these enzymes may be manipulated by introduction of nucleic acid molecules that direct or inhibit expression of such enzymes.

Figure 2:
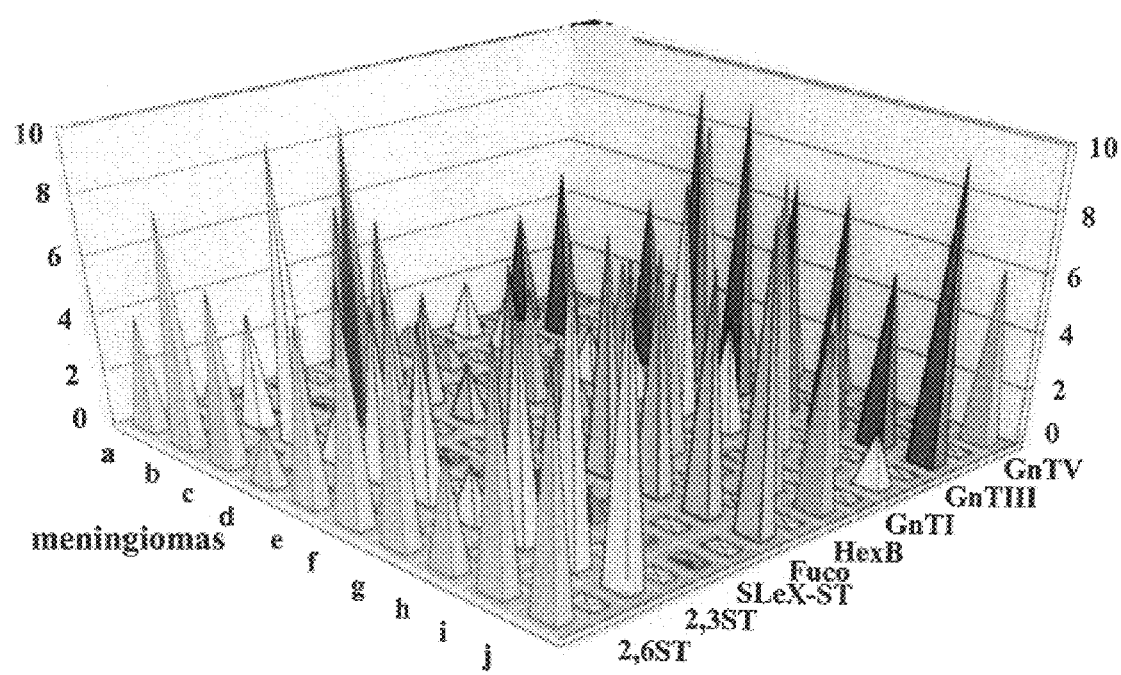
FIG. 2. Glyco-Enzyme mRNA Expression in Meningiomas.

Applicants have also studied the expression of glycosyltransferase enzymes in meningiomas (FIG. 2). The data indicate that the majority of meningiomas tested express relatively high levels of α2,6-ST, α2,3-ST, Fuco, and GnTIII; relatively moderate levels of HexB and GnTI; and relatively low levels of SLex-ST and GnTV. The reagents and methodologies of the present invention may be utilized to alter glycosylation and sialylation in meningioma by, for instance, transfecting into a meningioma an antisense construct against α2,6-ST, α2,3-ST, Fuco or GnTIII. Similarly, introduction of an expression vector encoding SLex-ST or GnTV such as that provided by the present invention into a meningioma provides an increased amount of enzyme in the cell resulting in alteration of glycosylation patterns. Either of the above methodologies will decrease tumorigenicity by, for example, decreasing adhesivity or increasing immunogenicity.

In practicing the present invention, it is advantageous to transfect into a cell a nucleic acid construct directing expression of a protein or nucleic acid product having the ability to alter expression of a glycosyltransferase. There are available to one skilled in the art multiple viral and non-viral methods suitable for introduction of a nucleic acid molecule into a target cell. Genetic manipulation of primary tumor cells has been described previously (Patel et al., 1994). Genetic modification of a cell may be accomplished using one or more techniques well known in the gene therapy field (*Human Gene Therapy* April 1994, Vol. 5, p. 543–563; Mulligan, R. C. 1993). Viral transduction methods may comprise the use of a recombinant DNA or an RNA virus comprising a nucleic acid sequence that drives or inhibits expression of a protein having sialyltransferase activity to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes but is not limited to a retrovirus or Sindbis virus. It is to be understood by those skilled in the art that several such DNA and RNA viruses exist that may be suitable for use in the present invention.

Adenoviral vectors have proven especially useful for gene transfer into eukaryotic cells (Stratford-Perricaudet and Perricaudet. 1991). Adenoviral vectors have been successfully utilized to study eukaryotic gene expression (Levrero, M., et al. 1991). vaccine development (Graham and Prevec, 1992), and in animal models (Stratford-Perricaudet, et al. 1992.; Rich, et al. 1993). The first trial of Ad-mediated gene therapy in human was the transfer of the cystic fibrosis transmembrane conductance regulator (CFTR) gene to lung (Crystal, et al., 1994). Experimental routes for administrating recombinant Ad to different tissues in vivo have included intratracheal instillation (Rosenfeld, et al. 1992) injection into muscle (Quantin, B., et al. 1992), peripheral intravenous injection (Herz and Gerard, 1993) and stereotactic inoculation to brain (Le Gal La Salle, et al. 1993). The adenoviral vector, then, is widely available to one skilled in the art and is suitable for use in the present invention.

Adeno-associated virus (AAV) has recently been introduced as a gene transfer system with potential applications in gene therapy. Wild-type AAV demonstrates high-level infectivity, broad host range and specificity in integrating into the host cell genome (Hermonat and Muzyczka 1984). Herpes simplex virus type-1 (HSV-1) is attractive as a vector system for use in the nervous system because of its neurotropic property (Geller and Federoff. 1991; Glorioso, et al. 1995). Vaccinia virus, of the poxvirus family, has also been developed as an expression vector (Smith and Moss, 1983; Moss, 1992). Each of the above-described vectors are widely available to one skilled in the art and would be suitable for use in the present invention.

Retroviral vectors are capable of infecting a large percentage of the target cells and integrating into the cell genome (Miller and Rosman. 1989). Retroviruses were developed as gene transfer vectors relatively earlier than other viruses, and were first used successfully for gene marking and transducing the cDNA of adenosine deaminase (ADA) into human lymphocytes.

It is also possible to produce a viral vector in vivo by implantation of a "producer cell line" in proximity to the target cell population. As demonstrated by Oldfield, et al. (1993), infiltration of a brain tumor with cells engineered to produce a viral vector carrying an effector gene results in the continuous release of the viral vector in the vacinity of the tumor cells for an extended period of time (i.e, several days).

In such a system, the vector is retroviral vector which preferably infects proliferating cells, which, in the brian, would include mainly tumor cells. The present invention provides a methodology with which a viral vector supplies a nucleic acid sequence encoding a protein having sialyltransferase activity to cells involved in a nuerological disorder such as brain cancer.

"Non-viral" delivery techniques that have been used or proposed for gene therapy include DNA-ligand complexes, adenovirus-ligand-DNA complexes, direct injection of DNA, $CaPO_4$ precipitation, gene gun techniques, electroporation, and lipofection (Mulligan, 1993). Any of these methods are widely available to one skilled in the art and would be suitable for use in the present invention. Other suitable methods are available to one skilled in the art, and it is to be understood that the present invention may be accomplished using any of the available methods of transfection. Several such methodologies have been utilized by those skilled in the art with varying success (Mulligan, R. 1993). Lipofection may be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl seine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

The cells may be transfected in vivo (preferably at the tumor site), ex vivo (following removal from a primary or metastatic tumor site), or in vitro. The cells may be transfected as primary cells isolated from a patient or a cell line derived from primary cells, and are not necessarily autologous to the patient to whom the cells are ultimately administered. Following ex vivo or in vitro transfection, the cells may be implanted into a host, preferably a patient having a neurological disorder and even more preferably a patient having a brain tumor. Genetic manipulation of primary tumor cells has been described previously (Patel et al. 1994). Genetic modification of the cells may be accomplished using one or more techniques well known in the gene therapy field (*Human Gene Therapy.* April 1994. Vol. 5, p. 543–563; Mulligan, R. C. 1993).

In order to obtain transition of the nucleic acid of the present invention within a target cell, a transcriptional regulatory region capable of driving gene expression in the target cell is utilized. The transcriptional regulatory region may comprise a promoter, enhancer, silencer or repressor element and is functionally associated with a nucleic acid of the present invention. Preferably, the transcriptional regulatory region drives high level gene expression in the target cell. It is further preferred that the transcriptional regulatory region drives transcription in a cell involved in a neurological disorder such as brain cancer. Transcriptional regulatory regions suitable for use in the present invention include but are not limited to the human cytomegalovirus (CMV) immediate-early enhancer/promoter, the SV40 early enhancer/promoter, the JC polyomavirus promoter and the chicken β-actin promoter coupled to the CMV enhancer (Doll, et al. 1996).

The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.). Examples of nucleic acid constructs usefull for practicing the present invention comprise a transcriptional regulatory region such as the CMV immediate-early enhancer/promoter, the SV40 early enhancer/promoter, the JC polyomavirus promoter, or the chicken β-actin promoter coupled to the CMV enhancer operably linked to a nucleic acid encoding a glycosyltransferase or sialyltransferase enzyme that is preferably α2,6-ST; α2,3-ST; SLex-ST; Fuco; HexB; GnTI; GnTIII or GnTV (FIG. 3). To generate such a construct, a nucleic acid sequence encoding the enzyme may be processed using one or more restriction enzymes such that certain sequences flank the nucleic acid. Processing of the nucleic acid may include the addition of linker or adapter sequences. A nucleic acid sequence comprising a preferred transcriptional regulatory region may be similarly processed such that the sequence has flanking sequences compatible with the nucleic acid sequence encoding the enzyme. These nucleic acid sequences may then be joined into a single construct by processing of the fragments with an enzyme such as DNA ligase. The joined fragment, comprising a transcriptional regulatory region operably linked to a nucleic acid encoding a glycosyltransferase or a sialyltransferase enzyme, may then be inserted into a plasmid capable of being replicated in a host cell by further processing using one or more restriction enzymes.

Administration of a nucleic acid of the present invention to a target cell in vivo may be accomplished using any of a variety of techniques well known to those skilled in the art. Such reagents may be administered by intravenous injection or using a technique such as stereotactic injection to administer the reagent into the target cell or the surrounding areas (Badie, et al. 1994; Perez-Cruet, et al. 1994; Chen, et al. 1994; Oldfield, et al. 1993; Okada, et al. 1996).

The vectors of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The dosage regimen for treating a neurological disorder disease with the vectors of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The pharmaceutically active compounds (i.e., vectors) of this invention can be processed in accordance with conventional methods of pharmacy to produce medicinal agents for administration to patients, including humans and other mammals. For oral administration, the pharmaceutical composition may be in the form of, for example, a capsule, a tablet, a suspension, or liquid. The pharmaceutical composition is preferably made in the form of a dosage unit containing a given amount of DNA or viral vector particles (collectively referred to as "vector"). For example, these may contain an amount of vector from about $10^3$–$10^{15}$ viral particles, preferably from about $10^6$–$10^2$ viral particles. A suitable daily dose for a human or other mammal may vary widely depending on the condition of the patient and other factors, but, once again, can be determined using routine methods. The vector may also be administered by injection as a composition with suitable carriers including saline, dextrose, or water.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A suitable topical dose of active ingredient of a vector of the present invention is administered one to four, preferably two or three times daily. For topical administration, the vector may comprise from 0.001% to 10% w/w, e.g., from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

While the nucleic acids and/or vectors of the invention can be administered as the sole active pharmaceutical agent, they can also be used in combination with one or more vectors of the invention or other agents. When administered as a combination, the therapeutic agents can be formulated as separate compositions that are given at the same time or different times, or the therapeutic agents can be given as a single composition.

The present invention may comprise elevation or depression of enzyme levels in cells expressing various amounts of enzyme. Introduction of an glycosyltransferase expression vector into a cell already expressing a high level of that enzyme may alter glycosylation patterns within that cell. Similarly, introduction of a nucleic acid construct that inhibits expression of such an enzyme in a cell expressing low levels of that enzyme may also serve to alter glycosylation patterns in that cell. Either of these methodologies may decrease the tumorigenicity of the cell by any of multiple mechanisms.

The reagents and methodologies of the present invention may be utilized to treat or prevent a variety of disorders in which glycosylation is involved. An example of such a disorder is cancer. Cancer is defined herein as any cellular malignancy for which a loss of normal cellular controls results in unregulated growth, lack of differentiation, and increased ability to invade local tissues and metastasize. Cancer may develop in any tissue of any organ at any age. Cancer may be an inherited disorder or caused by environmental factors or infectious agents; it may also result from a combination of these. For the purposes of utilizing the present invention, the term cancer includes both neoplasms and premalignant cells. A specific example of utilization of the present invention to treat brain cancer is provided herein Brain cancer is defined herein as any cancer involving a cell of neural origin. Examples of brain cancers include but are not limited to intracranial neoplasms such as those of the skull (i.e., osteoma, hemangioma, granuloma, xanthona, osteitis deformans), the meninges (i.e., meningioma, sarcoma, gliomatosis), the cranial nerves (i.e., glioma of the optic nerve, schwannoma), the neuroglia (i.e., gliomas) and ependyma (i.e., ependymomas), the pituitary or pineal body (i.e., pituitary adenoma, pinealoma), and those of congenital origin (i.e., craniopharygioma, chordoma, germinoma, teratoma, dermoid cyst, angioma, hemangioblastoma) as well as those of metastatic origin.

In one embodiment of the present invention, a method for decreasing the tumorigenicity or malignancy of a brain cancer cell comprising altering the expression of glycosylation of proteins produced by said cell, wherein the altered pattern of glycosylation is caused by the alteration of activity of glycosyltransferase within said cell is provided. Preferably, the glycosyltransferase is α2,3-ST glycosyltransferase, α2,6-ST glycosyltransferase, HexB glycosyltransferase, Fuco glycosyltransferase, GnTIII glycosyltransferase, GnTI glycosyltransferase, SLex-ST glycosyltransferase and GnTV glycosyltransferase. It is further preferred that the brain cell is a glioma or a meningioma cell. In one embodiment, altered activity of the glycosyltransferase is caused by the inhibition of the activity of α2,3-ST glycosyltransferase, HexB glycosyltransferase, SLex-ST glycosyltransferase or GnTIII glycosyltransferase. In another embodiment, altered activity of glycosyltransferase is caused by the inhibition of the activity of α2,3-ST glycosyltransferase, α2,6-ST glycosyltransferase, Fuco glycosyltransferase or GnTIII glycosyltransferase. In yet another embodiment, altered activity of the glycosyltransferase is caused by the inhibition of the activity of α2,6-ST glycosyltransferase, Fuco glycosyltransferase, GnTI glycosyltransferase or GnTV glycosyltransferase.

In another embodiment, the present invention provides a methodology for transfection of a functional nucleic acid sequence, preferably an antisense oligonucleotide, that inhibits expression of a protein having glycosyltransferase activity within a target cell. The antisense oligonucleotide may comprise a functional nucleotide sequence such as a 2',5'-oligoadenylate as described in U.S. Pat. No. 5,583,032. Using such an antisense oligonucleotide, expression of the protein having sialyltransferase activity may be inhibited by inhibition of transcription, destruction of the transcript encoding the protein or inhibition of translation of the protein from its transcript. Inhibition of glycosyltransferase activity may be caused by the hybridization of an anti-sense DNA specific to a target nucleic acid encoding for or involved in the expression of a glycosyltransferase. In one embodiment, the target nucleic acid sequence encodes α2,3-ST glycosyltransferase, HexB glycosyltransferase, SLex-ST glycosyltransferase and GnTIII glycosyltransferase. In another embodiment, the target nucleic acid encodes SLex-ST glycosyltransferase or GnTV glycosyltransferase. In yet another embodiment, the target nucleic acid encodes α2,3-ST glycosyltransferase, α2,6-ST glycosyltransferase, Fuco glycosyltransferase and GnTIII glycosyltransferase. Such a construct may be transfected into a glioma cell to inhibit the expression of a glycosyltransferase such as α2,3-ST, SLex-ST, HexB, or GnTIII. The resultant decrease in expression of these enzymes results in altered patterns of glycosylation, and, as described above, decreases tumorigenicity of the glioma.

Alteration of the activity of a glycosyltransferase may also be caused by the increase of activity of a glycosyltransferase. In one embodiment, the present invention comprises administration of a nucleic acid encoding α2,6-ST glycosyltransferase, Fuco glycosyltransferase, GnTI glycosyltransferase or GnTV glycosyltransferase. In another embodiment, the glycosyltransferase is SLex-ST glycosyltransferase or GnTV glycosyltransferase. In one embodiment, the increased activity of a glycosyltransferase may be caused by the stable transfection of an exogenous DNA encoding for a glycosyltransferase, expressibly linked to an inducible promoter, into a cell wherein the exogenous DNA encodes α2,6-ST glycosyltransferase, Fuco glycosyltransferase, GnTI glycosyltransferase and GnTV glycosyltransferase. In another embodiment, the exogenous DNA encodes SLex-ST glycosyltransferase and GnTV glycosyltransferase.

In another embodiment, the present invention provides an isolated nucleic acid sequence encoding for a recombinant, replication-deficient adenovirus and a glycosyltransferase, such as α2,3-ST glycosyltransferase, α2,6-ST glycosyltransferase, HexB glycosyltransferase, Fuco glycosyltransferase, GnTIII glycosyltransferase, GnTI glycosyltransferase, SLex-ST glycosyltransferase and GnTV glycosyltransferase is provided. And, in yet another embodiment, an isolated nucleic acid sequence encoding for a recombinant, replication-deficient adenovirus and a glycosyltransferase under transcriptional control of a regulator selected from the group consisting of CMV immediate-early enhancer/promoter, SV40 early enhancer/promoter, JC polyomavirus promoter, and chicken β-actin promoter is provided.

In another embodiment, the present invention provides a recombinant adenoviral particle containing a nucleic acid encoding for a glycosyltransferase such as α2,3-ST glycosyltransferase, α2,6-ST glycosyltransferase, HexB glycosyltransferase, Fuco glycosyltransferase, GnTIII glycosyltransferase, GnTI glycosyltransferase, SLex-ST glycosyltransferase and GnTV glycosyltransferase. In yet another embodiment, the expression of the nucleic acid encoding for the glycosyltransferase is under transcriptional control of a regulator selected from the group consisting of CMV immediate early enhancer/promoter, SV40 early enhancer/promoter, JC polyomavirus promoter, and chicken β-actin promoter.

In certain embodiments of the present invention, transfection of a cell is performed. In a preferred embodiment, the cell is involved in the causation of a neurological disorder such as brain cancer, Parkinson's disease or Alzheimer's disease. In a preferred embodiment, the cell is a cancer cell, and in a more preferred embodiment, the cell is a brain cancer cell. In certain embodiments, the present invention includes the transfer of a nucleic acid sequence encoding a protein having the ability to add a glycosyl moiety (i.e., glycosyltransferase) to a substrate protein. Preferably, the nucleic acid sequence encodes a glycosyltransferase enzyme. More preferably, the nucleic acid encodes α2,3-ST, α2,6-ST, SLeX-ST, Fuco, HexB, GnTI, GnTIII or GnTV. Even more preferably, the nucleic acid comprises a sequence encoding a glycosyltransferase that is under the transcriptional control of a transcriptional regulatory region which functions within a neural tissue or cell.

For instance, in certain embodiments of the present invention, a nucleic acid encoding a glycosyltransferase such as α2,6-ST, Fuco, GnTI or GnTV under the transcriptional control of a transcriptional regulatory region that functions in a glioma is transfected into a glioma cell. This results in increased expession of the encoded enzyme and may alter the patterns of glycosylation of certain proteins resulting in decreased adhesive potential or increased immunogenicity and, concomitantly, decreased tumorigenicity.

In another embodiment of the present invention, a target cell is transfected in vivo by implantation of a "producer cell line" in proximity to the target cell population (Culver, et al. 1994; Oldfield, 1993). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the product of nucleic acid of the present invention occurs. Preferably, expression results in either increased or decreased expression of a protein having glycosyltransferase or sialyltransferase activity. More preferably, the protein is α2,6-ST; α2,3-ST; SLex-ST; Fuco; HexB; GnTI; GnTIII or GnTV.

The present invention further provides a method for detecting the tumorigenicity or malignancy of a brain cell, comprising measuring the expression of glycosyltransferase within said cell. Any method for detection of the glycosyltransferase may be utilized including but not limited to assays for the presence or activity of the glycosyltransferase protein within a cell or assays for detecting nucleic acids encoding or involved in the expression of a glycosyltransferase. Detection of a nucleic acid encoding a glycosyltransferase may be accomplished by detection of glycosyltransferase mRNA using any of several techniques available to one skilled in the art such as northern blot (Alwine, et al. Proc. Natl. Acad. Sci. 74:5350), RNase protection (Melton, et al. Nuc. Acids Res. 12:7035), or RT-PCR (Berchtold, et al. Nuc. Acids. Res. 17:453). In one embodiment, the glycosyltransferase is selected from the group consisting of α2,3-ST glycosyltransferase, α2,6-ST glycosyltransferase, HexB glycosyltransferase, Fuco glycosyltransferase, GnTIII glycosyltransferase, GnTI glycosyltransferase, SLex-ST glycosyltransferase and GnTV glycosyltransferase. In another embodiment, detection of expression of the glycosyltransferase is accomplished by detection of nucleic acid sequences specific for glycosyltransferase.

In yet another embodiment, the present invention comprises a kit for determining the tumorigenicity or malignancy of a brain cell. The kit may comprise a panel of independent or paired nucleic acid molecules specific for the detection of the expression of specific nucleic acid sequences corresponding to specific species of glycosyltransferase. One embodiment of such a kit utilizes enzyme-mediated nucleic acid amplification such as the polymerase chain reaction (PCR) in which a pair of nucleic acid molecules (i.e., primers) that allow for amplification of a nucleic acid sequence encoding α2,3-ST glycosyltransferase, α2,6-ST glycosyltransferase, HexB glycosyltransferase, Fuco glycosyltransferase, GnTIII glycosyltransferase, GnTI glycosyltransferase, SLex-ST glycosyltransferase and GnTV glycosyltransferase. As illustrated in FIGS. 1 and 2, the levels of expression of glycosyltransferase enzymes differs in various tumor types and a kit allowing for determining such levels of expression may be utilized to predict or determine tumorigenicity of certain cell samples.

The following Examples are for illustrative purposes only and are not intended, nor should they be construed as limiting the invention in any manner. Those skilled in the art will appreciate that variations and modifications can be made without violating the spirit or scope of the invention.

EXAMPLES

Example 1
Expression of α2,3-sialyltransferase (α2,3-ST) in Glioma

The role of α2,3-ST in carcinogenesis remains unclear to those skilled in the art. Since α2,3-ST mRNA expression is detected in normal human fetal astrocytes, it is possible the α2,3-ST gene is under developmental regulation (Kitagawa, 1994). As gliomas synthesize various extracellular matrix glycoproteins such as fibronectin, collagens, vitronectin and tenascin (Rutka, 1988; Zagzag, 1995), it is also possible that α2,3-linked sialic acids are present on one or more of these proteins and may be involved in tumorigenicity.

A. Detection of α2,3-ST mRNA

To determine whether glioma cells and brain metastases express the α2,3-ST mRNA, northern blot analysis was performed. Thirty μg of total RNA per lane were used for northern analysis. Human α2,3-ST cDNA was cloned by using the reverse-transcriptase polymerase chain reaction (RT-PCR) and poly A+ RNA from U-373 MG cells based on the sequence reported previously (Kitagawa, 1994). A sense primer, 3'-CTGGACTCTAAACTGCCTGC-5' (bp 196–215; SEQ ID NO. 1) and an antisense primer, 5'-CCCAGAGACrrGTTGGC-3' (bp 524–508; SEQ ID NO. 2) were used. 30 pmol each of a sense primer corresponding to SEQ ID NO:1 and an antisense primer corresponding to SEQ ID NO:2 were utilized. The PCR amplification cycle consisted of denaturation at 94° C. for 40 seconds, annealing at 50° C. for 40 seconds and elongation at 71° C. for one minute. After 35 cycles, a 329 bp PCR product was subcloned into pT7 Blue T vector (Novagen, Madison, Wis.) and the sequence of the insert was confirmed by the dideoxy termination method (Sequenase, United State Biochemical, Cleveland, Ohio). The cDNA coding for human α2,3-ST cDNA was gel purified following Xba I and Bam HI digestion of the vector and used as the template.

Figure 4:
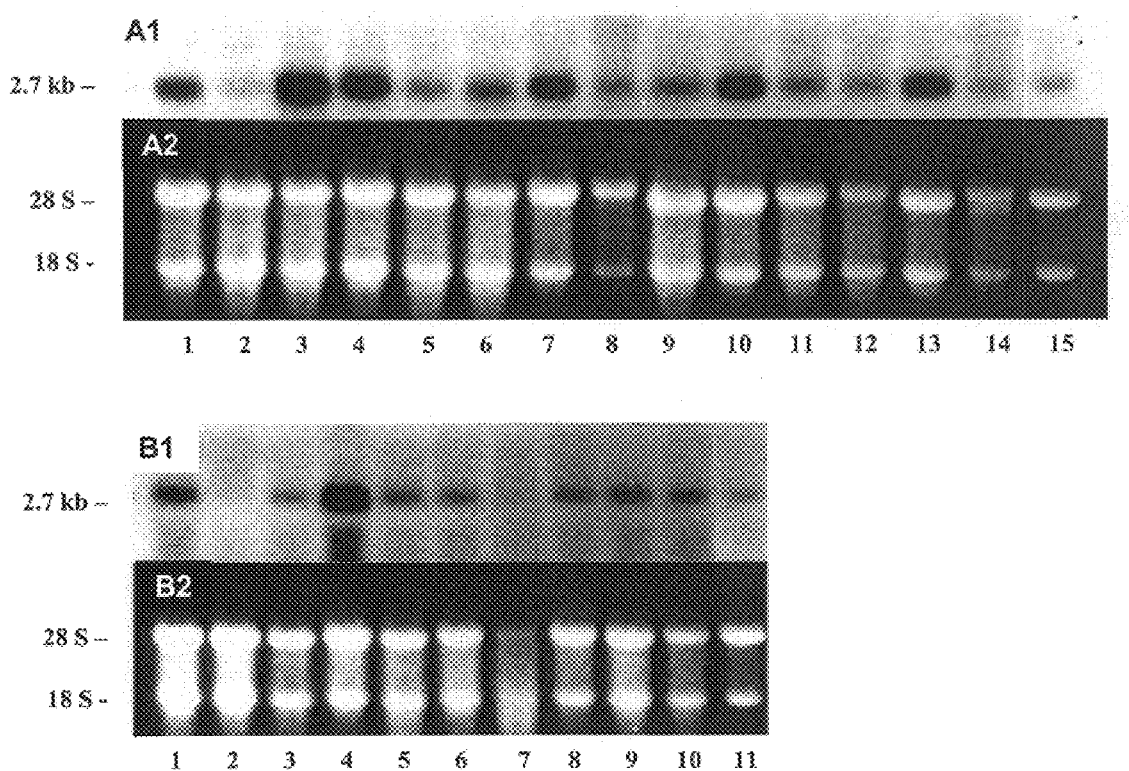
FIG. 4. α2,3-ST expression in glioma specimens (panels A1 and A2) and brain metastases (panels B1 and B2). Panels A1 and A2. Lane 1: normal human brain; lanes 2–14: clinical glioma specimens; lane 15: U-373MG human glioma cell line. Panels B1 and B2. Lane 1: normal human brain; lanes 2–10: clinical specimens of brain metastases; lane 11: U-373MC human glioma cell line. All glioma specimens expressed α2,3-ST mRNA (panels A1) and seven out of nine metastases expressed α2,3-ST mRNA (panel B1). Ethidium bromide staining of total RNA is shown in panels A2 and B2.

A panel of 13 surgical glioma specimens was analyzed in FIG. 4A: 1 astrocytoma grade II, 1 high-grade oligodendroglioma, 1 mixed glioma, 3 cases of astrocytoma grade III and 7 cases of astocytoma grade IV, ie. glioblastoma, (WHO Brain Tumor Classification, (Kepes, 1990)). Although the expression appeared variable, it is clear that 12 of 13 gliomas, as well as normal brain, expressed α2,3 ST mRNA. The only negative specimen was the grade II astrocytoma in FIG. 4, lane 2.

To determined if α2,3-ST is expressed in brain metastases, a panel of surgical specimens in FIG. 4B: 4 adenocarcinomas of lung origin, 3 adenocarcinomas of unknown origin, 1 papillary clear cell tumor of renal origin and one large cell neoplasm of unknown origin were also analyzed using the northern blot. The expression of α2,3-ST in glioma specimens is shown in the upper panel and brain metastases are shown in the lower panel. Seven of the nine samples demonstrate expression of α2,3 ST mRNA. Both negative samples (FIG. 4B. 1, lanes 2 & 7) were adenocarcinomas of unknown origin.

The expression of α2,3 ST mRNA was also detected in all human glioma and neuroblastoma cell lines examined, and was particularly high in cultured human fetal astrocytes (FIGS. 5A–D). All established human neural cell lines were maintained using Dulbecco's modified Eagle's medium (DMEM, containing 4.5 g/L glucose) supplemented with 10% heat-inactivated fetal bovine serum (Whittaker BioProducts, Walkersville, Md.). Fetal astrocytes were prepared according to a method described previously (Yong, 1992). These data indicate little difference in mRNA expression between glioma specimens and normal brain tissue, included as a control.

B. Detection of α2,3-ST protein

Figure 6:
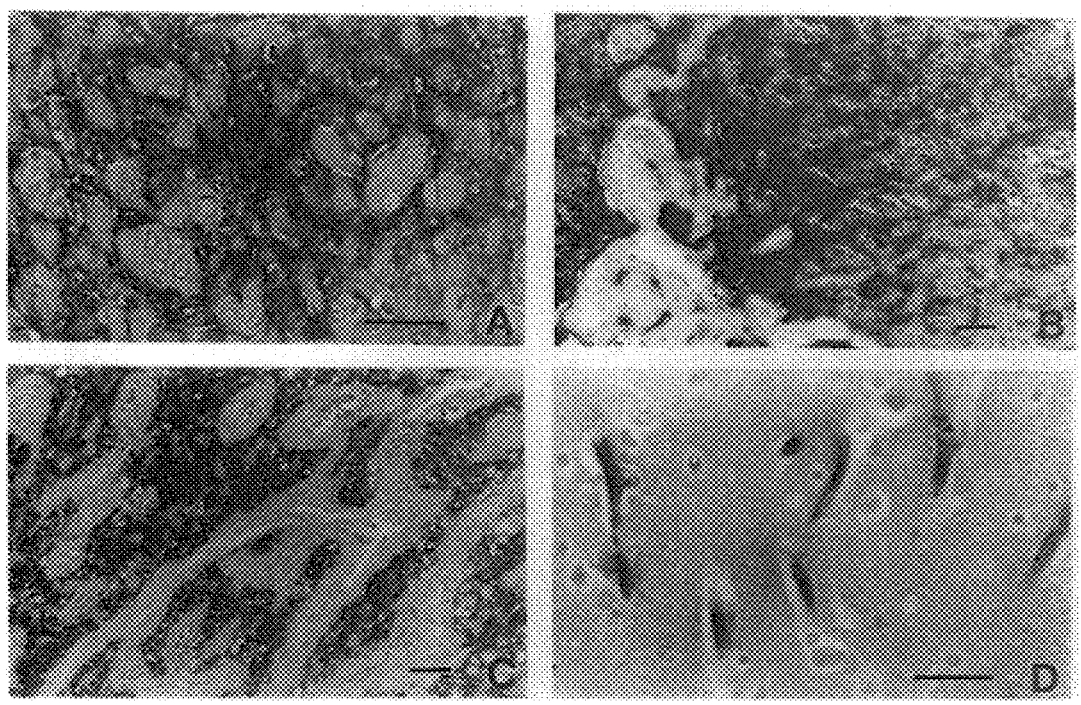
FIG. 6. Increased Maackia amurensis agglutinin lectin (MAA) staining in gliomas. Surfaces of glioblastoma cells (A), extracellular matrices between glioblastoma cells (B) and glioblastoma parenchyma (C) were heavily stained, while vasculatures within the tumors (B, C) remained negative. Positive MAA staining was observed in capillaries of normal cerebral cortex, but not in neurons or glial cells (D). Bars=50 µm.

In order to identify the cells expressing glycoproteins bearing α2,3-linked sialic adds, *Maackia amurensis* agglutinin (MAA) lectin staining was performed as described previously (Wang, 1988). The sections (6 μm thick) were dewaxed, hydrated and soaked in Tris-buffered saline (TBS, 150 mM NaCl, 50 mM Tris-HCl, pH 7.5) for 1–18 hours at 37° C., then incubated in 0.5% blocking reagent (Boehringer Mamnheim, Indianapolis, Ind.) in TBS for 45 mm. After rinsing twice with TBS and once with Buffer 1 (TBS with 1 mM MgCl$_2$, 1 mM MnCl$_2$, 1 mM CaCl$_2$, pH 7.5) for 10 mm each, digoxigenin-labeled MAA (Boehringer Mannheim) 10 μg/ml in Buffer 1 was overlaid for 1 h. After washing with TBS (3×10 mm), the sections were incubated with anti-digoxigenin Fab-conjugated with alkalie phosphatase (Boehlringer Mannheim) at concentration of either 0.75 or 1.5 U/ml TBS for 1 h After washing three times with TBS, BCIP/NBT solution (Signa, St. Louis, Mo.) was overlaid as chromogen for 3–40 mm. The sections were rinsed with deionized water and lightly counterstained with nuclear fast red. FIG. 6 illustrates the surfaces of glioblastoma cells (A), extracellular matrices between glioblastoma cells (B) and glioblastoma parenchyma (C) were heavily stained, while vasculatures within the tumors (B, C) remained negative. Positive MAA staining was observed in capillaries of normal cerebral cortex, but not in neurons or glial cells (D).

FIG. 6 shows that, while normal adult astrocytes and neurons were not stained with MAA, robust staining of glioblastoma tissue was observed. For example, a glioblastoma specimen (the specimen used in lane 4 of the Northern analysis shown in FIG. 4A) displayed heavy cell-surface staining of pleomorphic tumor cells (FIG. 6A) as well as at the invasion front proximal to the surrounding tissue (FIG. 6C). In another glioblastoma specimen (lane 10 in FIG. 4B), the matrices of clusters of undifferentiated small cells were stained with MAA, while proliferating endothelial cells derived from glomeruloid neovascularization were not stained (FIG. 6B); large vascular lumina in glioblastomas were rarely stained (data not shown).

The predominant MAA-positive cells found in normal adult cerebral cortex and white matter were vascular endothelial cells, suggesting tat α2,3-ST activity may play an important role in neovascularization. It should be noted that, because of the inherent limitations in the sensitivity of the detection method used in these studies, it is possible that normal adult astrocytes express α2,3-linked sialoglycoproteins at very low levels. Under the conditions employed in these studies, then, expression of α2,3-linked sialic acids (as demonstrated by MAA lectin histochemistry) could not be detected in adult human astrocytes; however, robust staining of fetal astocytes, normal adult brain vascular endothelial cells and primary human glioma specimens was observed. Consistent with such data, α-2,3-ST mRNA expression was observed in human fetal astrocytes, established glioma cell lines, and primary human glioma specimens. α2,3-ST mRNA was detected in whole brain tissue using northern blot analysis. However, lectin histochemical analysis with MAA revealed that only vascular endothelial cells were positively stained. Thus it can be concluded that α2,3-ST mRNA expression in normal adult brain is expressed in vascular endothelial cells and at very low levels, if at all, by normal adult glia.

The differential MAA lectin staining of glioma cell surfaces but not normal adult glia and the heavy MAA staining of glioma-associated extracellular matrices suggests the presence of glioma-associated glycoproteins bearing α2,3-linked sialic acids. α2,3-ST was also found in most of the metastases to the brain. These data indicate that α2,3-ST is found in abundant amounts in malignant brain tumor tissue. It is possible, therefore, that α2,3-ST plays an important role in metastases of tumor cells to the brain. One embodiment of the present invention, then, addresses this possibility by providing a therapeutic treatment comprising administration of reagents that inhibit the function or expression of α2,3-ST in a cell.

Example 2

Development of a Glioma Cell Line Expressing α2,6-ST

This α2,6-ST enzyme has been suggested to play an important role in the transformation, metastatic potential and differentiation of colon carcinomas (La Marer, 1992; Le Marer, 1995; Dall'Olio, 1995; Vertino-Bell, 1994; Bresalier, 1990; Sata, 1991). of such cells. In addition, pre-treatment of metastatic colon carcinoma cells with a sialyltransferase inhibitor results in a significant decrease in pulmonary metastases (Kijima-Suda, 1986). High α2,6-sialylation of N-acetyllactosamine sequences in ras-transformed fibroblasts has been reported to correlate with high invasive potential (La Marer, 1995). Also, increased sialylation of metastatic lymphomas results in reduced adhesion of such cells to extracellular matrix proteins (Dennis, 1982).

Applicants have previously examined the expression of α2,6-ST in a variety of human brain tumors (Kaneko, 1996; Yamamoto, 1995). Applicants did not observe α2,6-ST expression in gliomas or metastases to the brain. These results suggest that a lack of expression of α2,6-ST may correlate with an increased tumorigenicity of gliomas as well as increased potential for metastases of tumor cells to the brain. Additionally, the expression of α2,3-ST in malignant gliomas and other human brain tumor cells provides the possibility that alteration of α2,3-ST expression may alter tumorigenicity of such cells.

Glioma cells have been demonstrated to express extremely low levels of α2,6-ST enzyme in contrast to their normal glial cell counterparts. Based on the hypothesis that a decrease in α2,6-ST may increse the metastatic ability of such cells, one embodiment of the present invention provides a cell line with which that hypothesis may be explored. Such a cell line is a valuable research tool and potentially as part of a therpeutic modality with which a neurological disorder such as a brain tumor may be treated. U373 MG was chosen as a suitable cell line for transfections because it does not express α2,6-ST mRNA or cell-surface linked sialic acid-containing glycoproteins (Kaneko, 1996; Yamamoto, 1995). The methodology with which such a cell line has been developed is demonstrated below.

A. Cell Culture

The human glioma cell line, U373 MG (American Type Culture Collection (ATCC), Rockville, Md.) and all transfectants were maintained using Dulbecco's modified Eagle's medium (DMEM, containing 4.5 g/L glucose) supplemented with 10% heat-inactivated fetal bovine serum (Whittaker BioProducts, Walkersville, Md.) at 37° C. in a humidified 10% $CO_2$ incubator.

B. Transfections

Human glioma U373 MG cells were transfected with the 1.45 kb rat α2,6-ST cDNA (Weinstein, 1987). For the stable tractions it was inserted into the pcDNA3 expression vector (Invitrogen, San Diego, Calif.) at the EcoRI site. The orientation of the insert was confirmed by ApaI restriction digestion. The pcDNA3/α2,6-ST construct was then transfected into U373 MG cells using a cationic liposome system, DOTAP (Boeringer Mannhein, Indianapolis, Ind.). Putative transfectants were then selected by antibiotic resistance in cell culture medium containing 800 μg/ml G418. After 6 weeks of culture in the presence of G418, the remaining cells were tested for the presence of α2,6-linked sialoglycoproteins and α2,6-ST mRNA expression.

Figure 7:
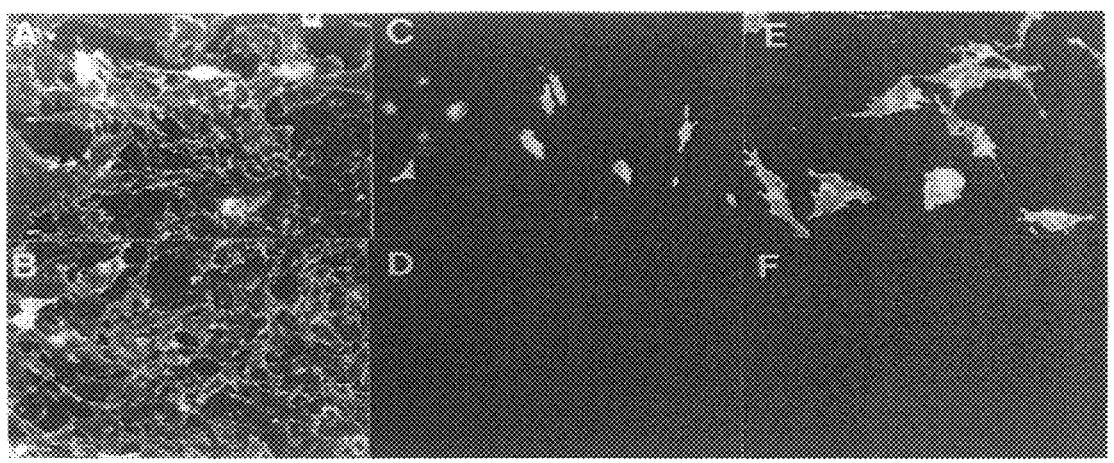
FIG. 7. Expression of α2,6-ST protein and α2,6-linked sialoglycoconjugates in transfected U373 MG cells. Transfected cells, prior to clonal selection, were grown on glass coverslips and immunofluorescence microscopy was performed as described in the Materials and Methods Section. The pcDNA3/~2,6-ST transfected cells (A, C, F) and pcDNA3 transfected cells (B, D, F) were stained with FITC-PHA-E (A, B) to detect bisecting type N-linked structures, anti-Q2,6-ST antibody (C, D), or FITC-SNA (F, F) to detect α2,6-linked sialoglycoconjugates.

C. Cell-surface α2,6-linked sialo-glycoproteins are expressed on the cell-surface of the stable transfectant The transfected cell population was stained for the presence of α2,6-ST protein and α2,6-linked sialoglycoconjugates on the cell surface. Thirty percent of the initial transfectants were positive for α2,6-ST and α2,6-linked sialoglycoconjugates (FIGS. 7, C and F). The transfected cells were also stained with PHA-E lectin, which stains bisecting-type complex oligosaccharides (Cummings, 1982). There was no difference in the PHA-E staining between transfected and non-transfected cells (FIGS. 7, A and B). These data indicate that there is little or no change in the branching pattern of the complex N-linked oligosaccharides after α2,6-ST transfection.

1. Detection by FITC-SNA staining

Expression of cell-surface α2,6-linked sialoglycoconjugates in transfected U373 MG cells was confirmed by staining with FITC-conjugated *Sambucus nigra* agglutanin (FITC-SNA; Vector laboratories, Burlingame, Calif.) to recognize the terminal Neu5Acα2,6Gal sequence using a modification of previously published methods (Lee, 1989). Preconfluent cells, grown on 12 mm glass coverslips, were fixed with 10% buffered formalin for 20 min at 25° C. followed by washing once with PBS. The fixed cells were incubated for 15 min at room temperature with PBS containing 10 μg FITC-SNA (Vector Labs, Burlingame, Calif.) and 1% BSA. After incubation, excess FITC-SNA was removed by washing the cover slips with PBS three times. The cells were mounted in 70% glycerin. Fluorescence microscopy was performed using a Nikon Model 401 Fluorescence Microscope. The pcDNA transfected cells were used as controls. FITC-PHA-E lectin (Vector Labs) was also used as a control to confirm that the branching of complex-type oligosaccharide structures in the transfectant remained unchanged after α2,6-ST transfection. This lectin has been reported to stain "bisecting-type", complex oligosaccharides (Cummings, 1982).

2. Detection by anti-α2,6-ST antibody staining

The transfected cells were plated onto 12 mm glass cover slips at 70% confluency, washed with PBS twice, and fixed with 10% buffered formalin for 20 min at room temperature.

The fixed cells were washed with PBS once for 3 min and incubated with 1% Nonidet P-40 (Sigma) in PBS for 10 min followed by washing twice with PBS for 3 min, all at room temperature. The cells were then incubated with affinity purified anti-rat α2,6-ST antibody (1:200 dilution) in 10% normal goat serum for 15 min at room temperature. This antibody was generously provided by Dr. Karen Collev (Univ. of Illinois at Chicago). After washing with PBS three times, the cells were incubated with FITC-labeled, anti-rabbit IgG (1:160 dilution; Sigma, St. Louis, Mo.) in PBS for 1 hr. The cells were washed with PBS three times to remove unbound secondary antibody and were mounted with 70% glycerin. Fluorescece microscopy was performed using a Nikon Model 401 Fluorescence Microscope. The pcDNA3 transfected cells were used as controls.

D. Subcloning of α2,6-ST transfected glioma cells

Sterile bacterial plates were coated aseptically with *Sambucus nigra* agglutanin (SNA)_(5 μg/ml), in 50 mM Tris-HCl, pH 9.5, incubated for 2 hrs at 20° C., and washed three times with 10 ml of 0.15 M NaCl. The plates were then incubated with 1 mg/ml BSA in PBS at 4° C. overnight to block non-specific binding of the cells. Well-dissociated transfected cells were incubated on the SNA coated plates for 10 miin at 20° C. Unbound cells were removed by washing the plate 10 times with PBS. Cells that remained bound to the plate were then allowed to grow by the addition of normal culture medium, and cloning rings (Belco Glass) were used to isolate individual clones.

Figure 8:
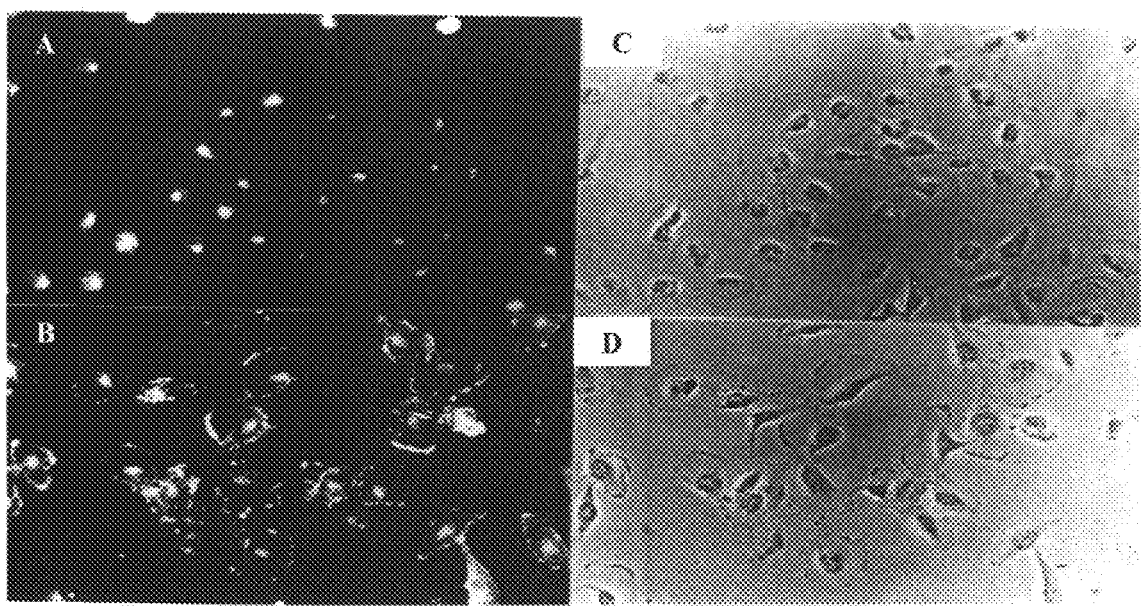
FIG. 8. Expression of α2,6-ST protein and α2,6-linked sialoglycoconjugates after subcloning. Fluorescence microscopy of clone #35. Clone #35cells were stained with anti-α2,6-ST antibody (A) or FITC-SNA(B). (C) and (D) are the corresponding phase contrast photomicrographs.

A total of 36 clones were isolated. Three of these clones were chosen for further analysis. Greater than 95% of the cells in each of these three clones were positive for SNA staining on the cell surface and stained affinity purified anti-α2,6-ST antibody. The intensity of staining, however, differed for each clone. The data for the most intensely stained clone (#35), is shown in FIGS. 8A and 8B. SNA staining of clone #35 was predominately on the cell surface but some cytoplasmic staining was also observed (FIG. 8B). Anti-α2,6-ST staining was localized to a perinuclear intracellular organelle, consistent with Golgi staining (FIG. 8A). The morphology of this clone is more round and less dendritic than the initial transfectants or controls (FIGS. 8, B and D).

E. Detection of α2,6-ST mRNA in transfectants

Northern analysis was performed to detect the expression of α2,6-ST mRNA in the tansfectants. Total RNA was isolated from parental U373 MG cells and transfectants using guanidium isothiocyanate (Chomczynsli, 1987) followed by CsCl$_2$ centrfugation (Chirgwin, 1979). 20 μg of total RNA per lane was electrophoresed in a formaldehyde-agarose gel and transferred to Duralon nylon membranes (Stratagene, La Jolla, Calif.). After UV cross-lining, blots were hybridized with a $^{32}$P-radiolabeled rat α2,6-ST cDNA probe synthesized by using a random priming kit (Stratagene, La Jolla, Calif.) and QuikHyb solution (Stratagene, La Jolla, Calif.). After washing at 60° C., the blot was exposed to X-OMAT film (Kodak, Rochester, N.Y.) for 16 hours and the film was then developed. Under these stringent conditions, the rat α2,6-ST cDNA probe only weakly cross-hybridized with the human transcript (data not shown).

The expression of rat α2,6-ST mRNA in the transfectants is demonstrated in FIG. 9A. A 2.1 kb transcript was detected in cells transfected with pcDNA3/α2,6-ST but not in parental cells or pcDNA3 transfected controls. In addition to message expression, α2,6-ST enzyme activity was determined in each of the isolated clones. The relative enzyme activity correlated well with the level of message expression (FIG. 9C). Clone #35 expressed the highest amount of α2,6-ST mRNA and also had the highest relative enzyme activity. Similarly, clone #24 expressed the least amount of message and had the lowest relative enzyme activity. Consistent with the highest level of message and enzyme activity, clone #35 also stained the most intensely with SNA indicating a high level of α2,6-linked sialoglycoconjugates on the cell surface.

F. Detection of α2,6-ST enzyme activity in transfectants

The α2,6-ST enzyme activity of the transfectants was measured as described by Paulson, et al. (1990) using the sugar nucleotide donor, CMP-($^{14}$C)NeuAc (6200 dpm/nmol; NEN/DuPont, Wilmington, Del.) and asialo-α1-acidic glycoprotein (50) kg/reaction mixture; Sigma, St. Louis, Mo.) as the acceptor. A whole cell extract was used as the enzyme source and the enzyme reactions were run for 30 mm at 37° C. and terminated by dilution into 1 ml of ice-cold 5 mM sodium phosphate buffer, pH 6.8. $^{14}$C-labeled protein products were immediately separated from unincorporated CMP-($^{14}$C)NeuAc by Sephadex G-50 column chromatography and quantitated using a Beckman LS 60005E liquid scintillation spectrometer.

Example 3

Effects of α2,6-ST expression on glioma a cell behavior in vitro

Integrins are a superfamily of transmembrane receptors that participate in cell-cell and cell-matrix interactions (Juliano, 1993; Hynes, 1992; Ruoslahti, 1992; Yamada, 1992). They are heterodimeric glycoproteins in which one of at least 14 α subunits associate with one of at least 8 β subunits to form a functional receptor (Ruoslahti, 1992). Most of the integrins that mediate adhesion to extracellular matrix components contain a common β1 component.

It is understood by those skilled in the art that glycosylation of integrin receptors is important for their function. Decreased sialylation of the β1 integrin subunit has been correlated with decreased adhesiveness and metastatic potential (Kawano, 1993). Furthermore, the ability of α5β1 receptors to form functional heterodimers depends on the presence of N-linked oligosaccharides (Zheng, 1994). Human fibroblasts cultured in the presence of 1-deoxymannojirimycin (DNJ) expressed incompletely glycosylated FN receptors and FN adhesion was greatly reduced (Akiyama, 1989). Adhesion to fibronectin and collagen were reduced more than 50% by treatment of colon carcinoma cells with DNJ (von Lampe, 1993). The α6β1-dependent binding of B16/F10 melanoma cells to laminin was nearly abolished when cells were treated with tunicamycin (Chammas, 1993). Furthermore, enzymatic deglycosylation of the α5β1 integrin receptor abolished its ability to bind to FN (Zheng, 1994).

The interaction of integrins with extracellular matrix components not only provides a structural link with the matrix but also gives rise to biochemical signals. Adhesion to and spreading on extracellular matrix results in the tyrosine phosphorylation of several focal adhesion proteins, including paxillin, focal adhesion kinase (p125$^{fak}$; FAK), and tensin (Richardson, 1995; Rosales, 1995; Clark, 1995; Schuppan, 1994). The phosphorylation of FAK is a key component of integrin-mediated adhesion and migration (Richardson, 1995; Rosales, 1995). Activation of both FAK and multiple signaling pathways are required for the appearance of strong cell adhesion, the turnover of focal adhesion sites (Schwartz, 1994; Sankar, 1995). Thus, alteration of integrin function or the signaling mechanisms associated with integrins may alter the adhesion properties of the cell.

DiMilla et al. (1991) and Lauffenberger (1989) have developed theoretical models demonstrating an inverted U-shaped relationship between cellular adhesivity and migration. A reduction in cellular adhesivity brought about by, for example, an alteration in integrin glycosylation, could either enhance or retard cell migration depending upon the initial strength of adhesion between a cell and its substratum. Experimental studies by several groups support this hypothesis: DiMilla et al. (1993) found that an optimal adhesiveness exists for muscle cell migration on collagen; Albeda (1993) and Wu et al. (1994), showed concentration-dependent, inhibitory and enhancing effects of an integrin-binding inhibitor on cell motility (Bresalier, 1990); and Keely et al. (1995), reported that cell motility of mammary cells across collagen-coated filters was increased only in those clones with intermediate levels of adhesion to collagen (see also Akiyama, 1989). Thus, a highly adhesive fibroblast with increased α2,6-sialylated cell-surface glycoconjugates, and reduced adhesivity to fibronectin, would be more invasive (La Marer, 1995). Thus, alteration of a cell's adhesive properties may represent a useful method with which to treat a disease, such as cancer.

A. Invasivity

Figure 10:
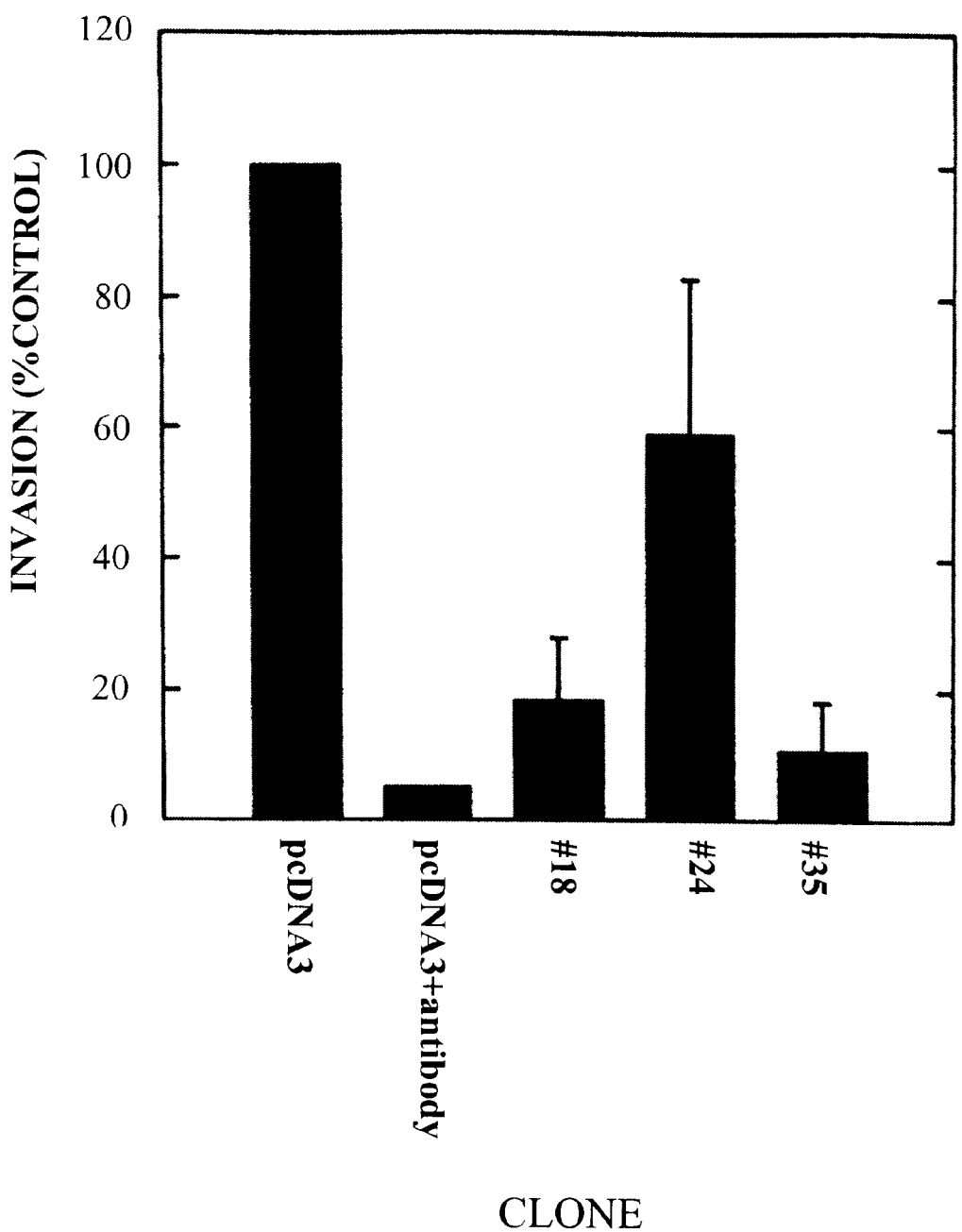
FIG. 10. In vitro invasion assay of the U373 MG/α2,6ST transfectant. Biocoat Matrigel Invasion Chambers (Collaborative Research, Bedford, Mass.) were used to evaluate the relative invasivity of the transfected subclones compared to pcDNA3 "mock" transfected controls. The data is an average of two separate experiments done in triplicate. Values did not vary by more than 10%.

Invasivity of the U373 MG/α2,6-ST transfected sub-clones (clones #18, #24 and #35) was examined using a commercial membrane invasion culture system (FIG. 10; Paulus, 1994; Hendrix, 1989). Biocoat Matrigel Invasion Chambers (Collaborative Research, Bedford, Mass.) consist of two compartments separated by a filter precoated with Matrigel (contains: laminin, type IV collagen, entactin and heperan sulfate). Cell invasion is measured by counting the number of cells passing to the opposite side of the filter via 8 micron pores. $4 \times 10^4$ cells were plated into the upper chamber and incubated for 24 hr. 0.5 ml of U373 MG-cell conditioned medium was placed in the lower compartment to facilitate chemoattraction (Hendrix, 1989). Cells that migrated through the Matrigel and through the filter were fixed in 10.!% formalin and stained with hematoxvlin. The membranes were mounted on glass slides and the cells counted (Paulus, 1994).

Figure 9:
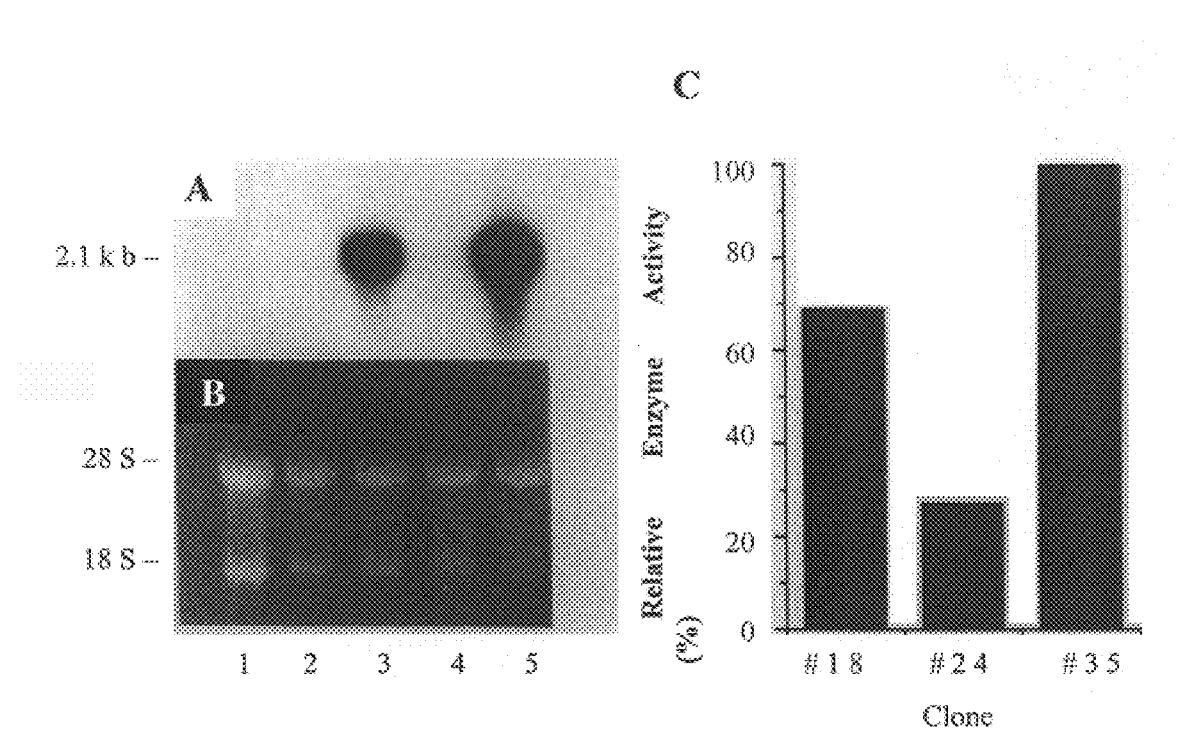
FIG. 9. Expression of α2,6-ST mRNA and enzyme activity In U373 MG/α2,6-ST clones. Total RNA was isolated from parental glioma U373 MG cells, pcDNA3 transfected cells, and three pcDNA3/α2,6-ST transfected clones (#18, #24, #35). 20 µg of total RNA per lane was electrophoresed. The 1.45 kb rat α2,6 ST cDNA was used for Northern analyses (panel A). In order to assess α2,6-ST expression caused by transfection artifacts, pcDNA3-transfected U373 MG cells were used as a control. Panel A. Lane 1, parental U373MG cells; lane 2, U373 MG cells transfected with pcDNA3; lane 3, pcDNA3/α2,6-ST transfected clone #18; lane 4, clone #24; lane 5, clone #35. Total RNA staining by ethidium bromide is shown in panel B. Panel C. Relative α2,6-ST enzyme activity expressed by the three transfected clones. Enzyme activity was determined as described below. The data was normalized to the highest expressing clone, #35. α2,6-ST enzyme activity was not detected in the parental or in the pcDNA3 transfected cells.

All data were normalized to pcDNA3 transfected cells. The invasivity of clones #18 and #35 were reduced to less than 20% of control values (FIG. 10). The invasivity of clone #24 was only reduced to 60% of the control values. These data appeared to correlate with the expression of enzyme activity in these clones (FIG. 9). Anti-α3 antibody was used to determine if α3β1 integrin was involved in the invasion process. Anti-α3 antibody was able to completely abolish the invasion of control pcDNA3-transfected cells in this assay.

B. Adhesion

Cell adhesion to defined matrix components was accomplished as previously described (Mosmann, 1994). Flat-bottomed, polystyrene, 24-well plates were incubated overnight at 4° C. with 40 μg/250 μl/well of an extracellular matrix substrate. Human fibronectin, human collagen type I, human laminin or human vitronectin (Collaborative Research, Bedford, Mass.) was used as a substrate. Plates were washed with 500 ml of 1.0% BSA in PBS twice to remove unbound extracellular matrix proteins and also to block any remaining reactive surfaces. Non-specific cellular binding was determined using wells coated only with 1.0% BSA. After washing the plates with PBS, $5 \times 10^4$ cells/well in 250 μl of DMEM were plated and the cells were incubated at 37° C. for 10 min or 30 min for attachment to the fibronectin substrate. After washing off non-adherent cells, 25 μl of 3-(4,5-diethylthiazol-2-yl)-2,5-diphenyl tetrazolium bromide (MTT, 5 mg/ml) was added to the culture, incubated for 3 hrs, and then 250 μl of acidic isopropanol (0.1N HCl in isopropanol) was added and mixed completely. Optical density (570 nm minus 630 nm) was measured to evaluate cells attached to the substrate. The cells without the washing procedure were used as 100%.

Figure 11:
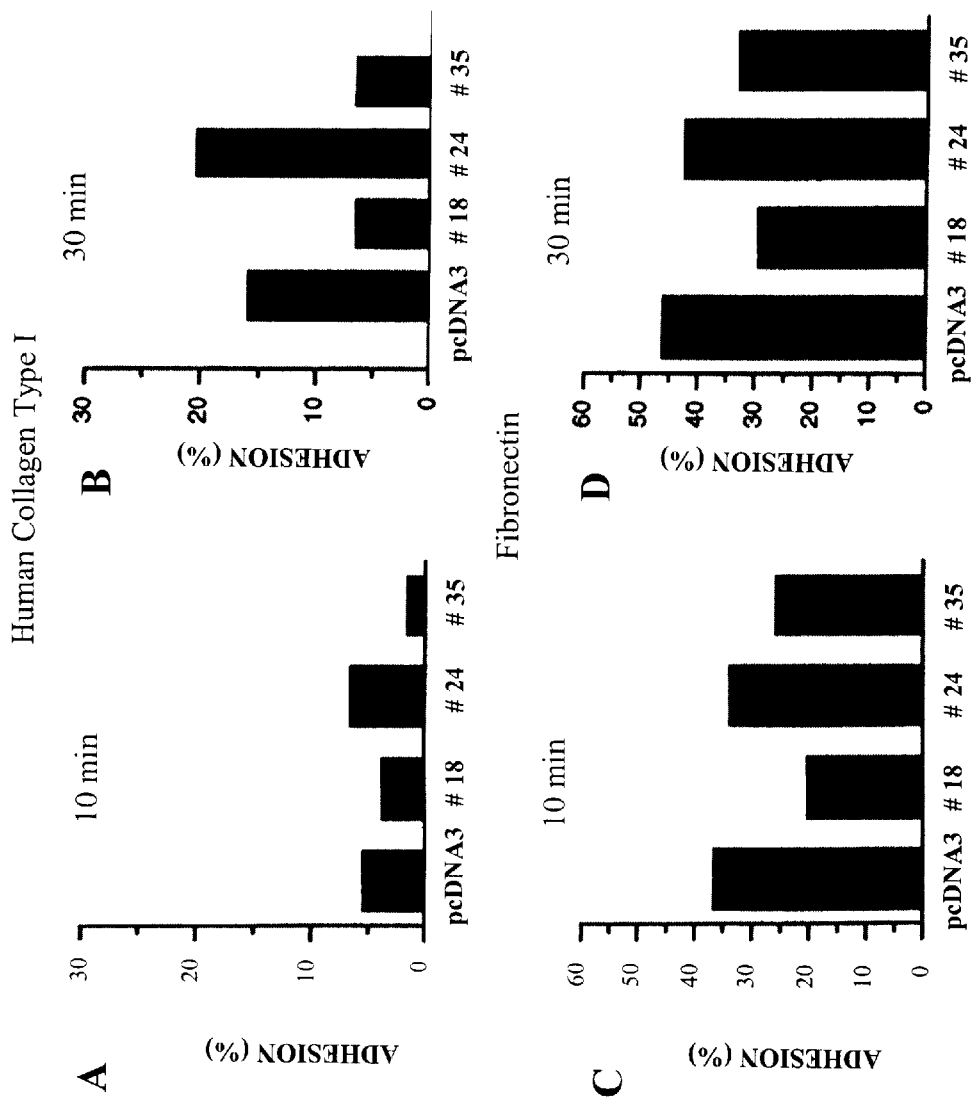
FIG. 11. In vitro adhesion assay of the U373 MG/α2,6ST bsfectant. Human fibronectin or collagen type I coated 24-well plates were used to evaluate the relative adhesion of three transfectants (clones #18, #24, #35). Compared to a pcDNA3 "mock" transfected control, the transfectants showed a reduction in adhesion to both fibronectin substrate and collagen type I. These data are the average of three values taken from a representative experiment and did not vary by more than 10%.

The U373 MG cells used in these studies express the α3β1 integrin as their only integrin (data not shown). This integrin has been reported to bind type I collagen, fibronectin, and laminin (Ruoslahti, 1994). The ability of the transfected clones to adhere to these extracellular matrix components was compared to that of untransfected U373 MG cells and pcDNA transfected U373 MC cells. Adhesion to a vitronectin substrate was also examined as a non-α3β1-mediated adhesion control. Adhesion was examined after 10 or 30 min incubation of the cells on the coated wells using a colorimetric assay (Kaneko, 1996). At 10 or 30 min incubation, approximately 40–50% of the control cells adhered to fibronectin (FIGS. 11C and 11D) or laminin substrata. On the collagen coated wells (FIGS. 11A and 11B), only 5% adhesion of the control cells was detected at 10 mm. This increased to 10–20% adhesion after 30 min. These data suggested that the kinetics of adhesion to type I collagen were different than that to fibronectin or laminin. A marked reduction in adhesion to both fibronectin and type I collagen substrata was observed with α2,6-ST transfected clones (FIG. 11) that expressed high amounts of α2,6-ST message and activity (FIG. 9). The reduction in adhesion to fibronectin was observed at both 10 and 30 min incubation. Consistent with the different binding kinetics to collagen, reduced adhesion of the transfectants to type I collagen was best observed at 30 mm. The reduction in adhesion of the transfectants was correlated with the degree of α2,6-ST expression and inhibition of invasivity (FIG. 10). Little difference was observed when laminin or vitronectin were used as a substrate (data not shown). These data suggested that α2,6-ST transfection of human glioma cells resulted in differential effects on the adhesion of these cells to different extracellular matrix components.

C. Sialylation

A marked reduction in adhesion to a fibronectin or collagen type I substrate was found in α2,6-ST transfected cells (FIG. 11), and decreased adhesion was correlated with the degree of α2,6-ST expression (FIG. 9). The effect of the gene transfection on the level of α3β1 integrin protein was determined in order to rule out the possibility of altered receptor expression as an explanation for the changes in adhesion.

Figure 12:
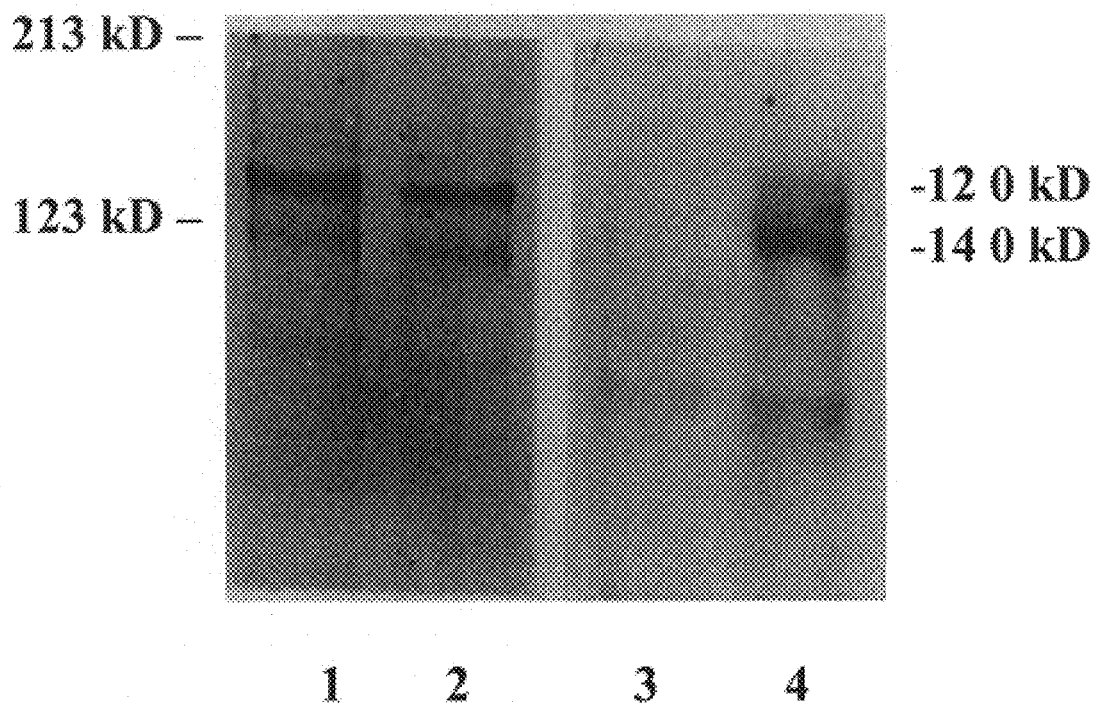
FIG. 12. α2,6-inked sialylation α3β1 integrin in the transfectant.

Clone #18 cells and U373 MC/pcDNA3 cells were incubated with methionine-free DMEM and 2 μCi/ml $^{35}$S-methionine for 16 hrs, and the cells were harvested. The membrane fraction was isolated, and solubilized with 1% NP-40 in 50 mM Tris-HCl, pH 7.6 containing proteinase inhibitors. 300 μg of solubilized proteins were used for immunoprecipitation with 20 μl anti-VLA3 monoclonal antibody (Novocastra, clone VM-2) followed by rabbit anti-mouse IgG and Protein A-agarose adsorption. Immunoprecipitated proteins were solubilized with 2% SDS and were loaded on a 6% SDS-polyacrylamide gel. After electrophoresis, the gel was dried and exposed to X-ray film (FIG. 12, lanes 1 and 2). The immunoprecipitated proteins were also transferred to a PVDF membrane after electrophoresis and stained with SNA lectin to detect α2,6-linked sialic acids (FIG. 12, lanes 3 and 4). Anti-VLA3 antibody recognizes the 140 kD α3 integrin subunit and co-immunoprecipitates a 120 kD protein, which is consistent with β1 subunit. α2,6-linked sialylation of α3β1 integrin molecules was detected in the transfectant but not in control cells.

Similar amounts of $^{35}$-labeled α3β1 integrin were immunoprecipitated from both the control and transfected cells (FIG. 12, lanes 1 and 2). The anti-VLA3 antibody used for this experiment directly recognizes the 140 kD α3 subunit and co-immunoprecipitates an 120 kD protein which is consistent with β1 subunit. These data indicated that there were no large differences in the levels of either the α3 or β1 protein.

The presence of α2,6-linked sialylation on the immunoprecipitated α3β1 integrin receptor in the transfected cells was determined by SNA staining. Abundant SNA staining of both subunits was detected in the transfected cells, while no SNA staining was observed in control cells (FIG. 12, lanes 3 and 4). These data indicated that α2,6-linked sialylation was present on the α3β1 integrin.

D. Tyrosine phosphorylation

The reduction in adhesion to fibronectin or collagen type I substratum suggested alteration in the ability of α2,6-sialylated integrins to bind. Binding of integrin receptors to their ligands stimulates tyrosine phosphorylation (Richardson, 1995) as well as adhesion to the extracellular matrix. Integrin-mediated protein tyrosine phosphorylation was examined in the transfected clones.

Equal amounts of whole cell lysate (50 μg protein) obtained from the transfected clones and controls were analyzed by SDS-PAGE followed by Western blotting using anti-phosphotyrosine antibody (Upstate Biotechnology, Lake Placid, N.Y.) as follows. The three subclones and pcDNA3 transfected control cells were incubated in fibronectin-coated flasks for 10 (FIG. 13A) or 30 min (FIG. 13B), and unattached cells were removed by washing three times with cold PBS. The attached cells were then solubilized with 200 μl of lysis buffer. The lysate was centrifuged at 12,000×g for 5 min to eliminate non-soluble material. An equal amount of protein (50 μg) from each sample was loaded on a 10% SDS-polyacrylamide gel. After electrophoresis, the proteins were transferred to a PVDF membrane, and the membrane was incubated with 3% non-fat milk at 21° C. for 30 min. Anti-phosphotyrosine antibody (Upstate Biotechnology) was then added at 1/1000 dilution and incubated at 21° C. for 1 hr. The membrane was then washed three times with PBS containing 0.05% Tween 20, and the antibody-bound proteins were detected using an BCL kit (Amersham).

Figure 13:
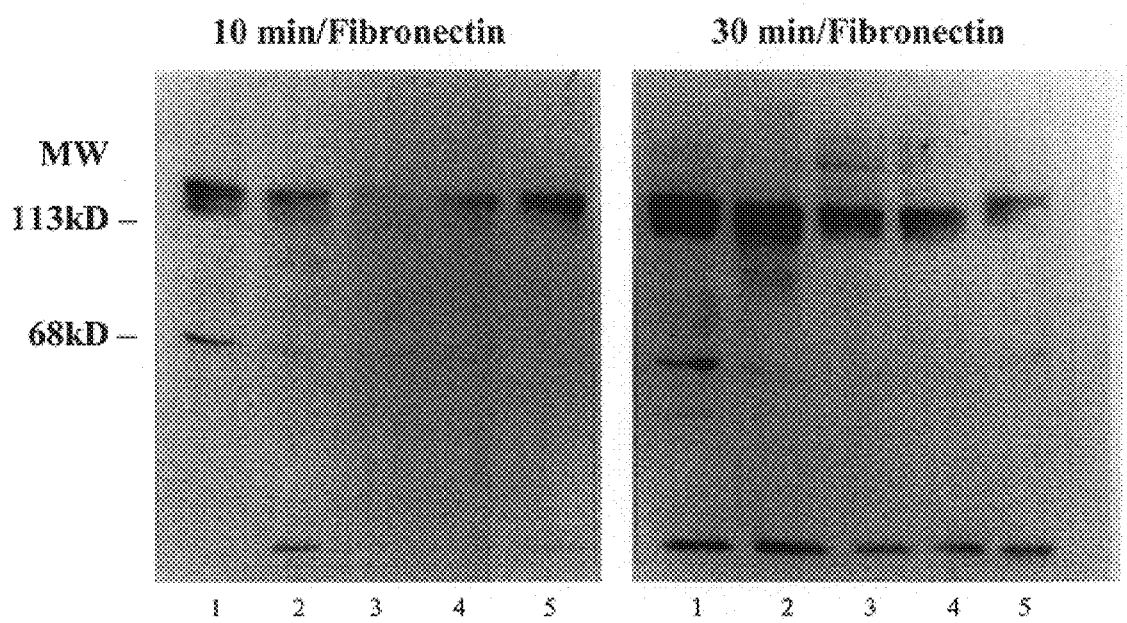
FIG. 13. Adhesion-mediated protein tyrosine phosphorylation in the transfected clones.

The qualitative pattern of phosphorylated proteins in each of the clones was identical to those of parental U373 MG or U373 MG/pcDNA3 cells (FIG. 13). The quantity of tyrosine phosphorylation in the transfected clones, however, was much less than either of the controls (FIG. 13). These results suggested that integrin mediated signaling was also inhibited by α2,6-linked sialylation. One of the phosphorylated proteins has a molecular mass of 125 kD, consistent with focal adhesion kinase (p125$^{fak}$). Focal adhesion kinase is a key tyrosine kinase involved in integrin mediated signal transduction (Richardson, 1995).

Figure 14:
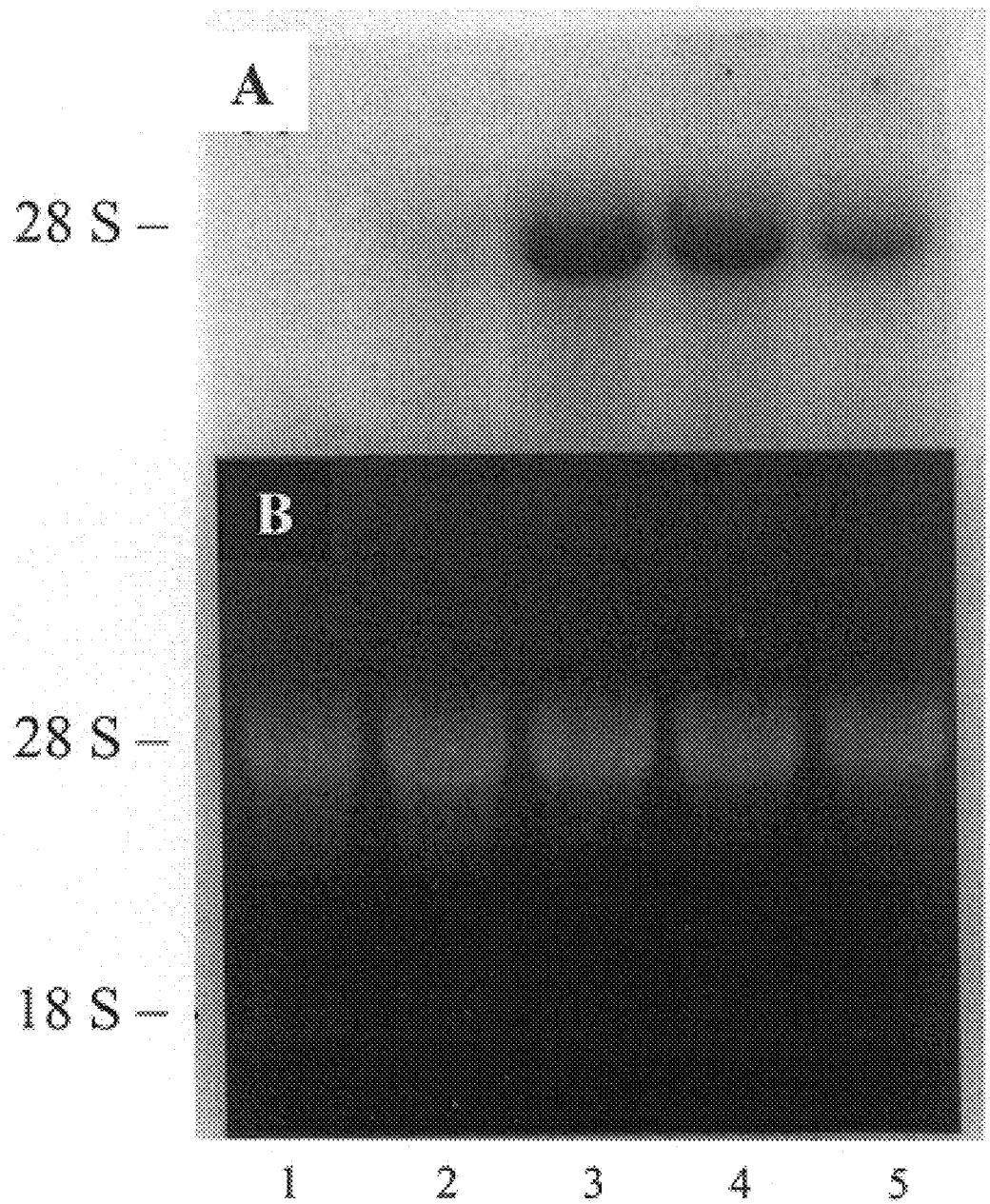
FIG. 14. Induction of focal adhesion kinase p125$^{fak}$ mRNA expression in α2,6ST transfected U373 MG.

The reduction of adhesion-mediated protein tyrosine phosphorylation may be due to reduced expression of integrin-dependent signaling molecules, such as p125$^{fak}$, in the transfected clones. To test this hypothesis, the expression of focal adhesion kinase p125$^{fak}$ mRNA was examined by northern analysis (FIG. 14). Northern analysis was performed with a human FAK cDNA probe (FIG. 14, panel A). Human FAK cDNA was cloned by using the reverse-transcriptase polymerase chain reaction (RT-PCR) and poly A+ RNA from U-373 MG cells. A sense primer, ATG-GCAGCTGCTTACCTTGACC (bp 233–254; SEQ ID NO:3) and an antisense primer, TTCATATffCCACTC-CTCTGG (bp 601–571; SEQ ID NO:4) were used (Scirrmacher, 1982; Reboul, 1990). 30 pmol each of a sense primer corresponding to SEQ ID NO:3 and an antisense primer corresponding to SEQ ID NO:4 were utilized. The PCR amplification cycle consisted of denaturation at 94° C. for 40 seconds, annealing at 50° C. for 40 seconds and elongation at 71° C. for one minute. After 35 cycles, a 369 bp PCR product (bp 233–601) was cloned into pT7 Blue T vector (Novagen, Madison, Wis.) and the DNA sequence of the insert was confirmed by the dideoxy termination method. The FAK cDNA was isolated from the gel after Xba I and Bam HI digestion of the vector and used as the template. 20 μg of total RNA per lane was electrophoresed for the analysis. Lane 1, U373 MG cells; lane 2, U373 MG cells transfected with pcDNA3; lane 3, pcDNA3/α2,6-ST transfected clone #18; lane 4, clone #24; lane 5, clone#35. Total RNA staining by ethidium bromide is shown in FIG. 8, panel B.

All transfected clones showed a marked increase (approx. 10-fold) of p125$^{fak}$ mRNA expression. p125$^{fak}$ protein was also increased in these subdones (data not shown) compared to controls. These results suggested that, despite the increased expression of p125$^{fak}$ in the transfected cells, integrin-mediated stimulation of tyrosine phosphorylation was greatly inhibited.

E. Actin cytoskeletal assembly and focal adhesion formation

The integrin β subunit is primarily involved in integrin-mediated signaling Rosales, 1995). This signaling includes integrin-mediated tyrosine phosphorylation of cytoplasmic proteins, such as focal adhesion kinase p125$^{fak}$ and reorganization of integrin-cytoskeletal assemblies. The decrease in adhesion mediated phosphorylation or the increased expression of p125$^{fak}$ may affect integrin and cytoskeletal assemblies including focal adhesion plaques and actin cytoskeletal assembly in the cells.

Figure 15:
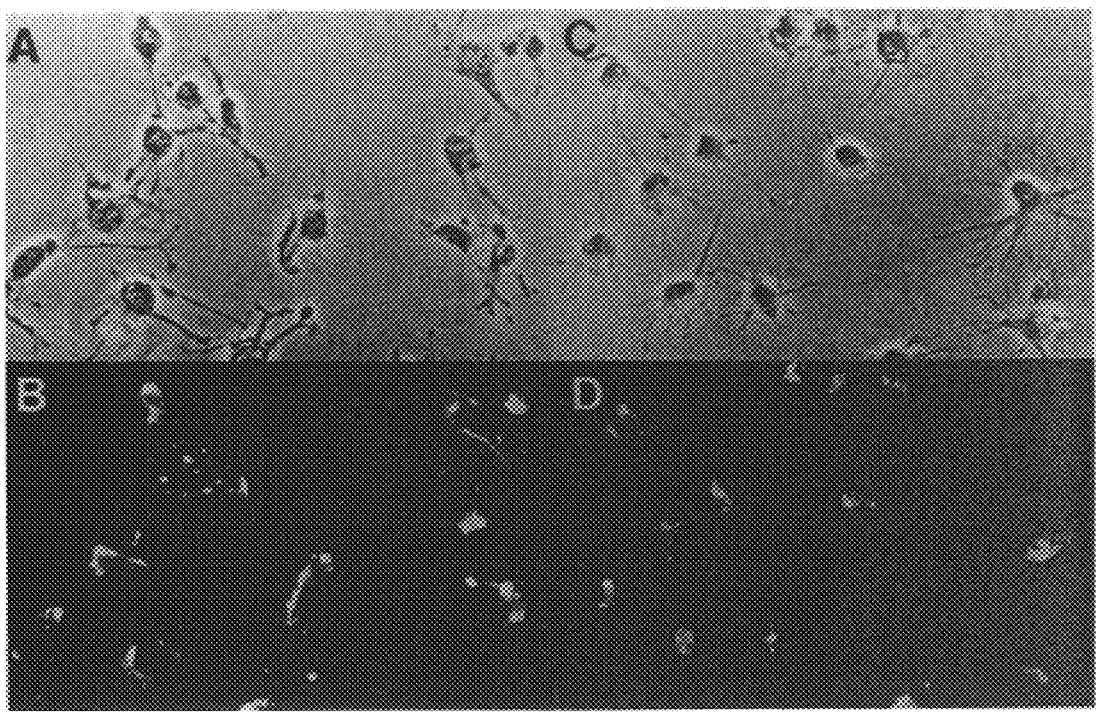
FIG. 15. Alteration of actin cytoskeletal assembly and focal adhesion sites in the transfected cells.

Human glioblastoma, U373 MG, cells transfected with either pcDNA3 (FIGS. 15A and 15B) or pcDNA3/α2,6ST (Clone #18, FIGS. 15C and 15D) were plated on fibronectin-coated cover slips and incubated overnight with DMEM containing 10% FBS. Cells were treated with 1.25 IU/ml cytochalasin D for 1 hr and then fixed with cold methanol for 15 min. After blocking with 10% normal goat serum, the cells were incubated with anti-actin polyclonal antibody (Sigmna, St. Louis, Mo.) at 1:100 dilution for 15 min at room temperature. After washing with PBS three times, the cells were incubated with FITC-labeled, anti-rabbit IgG (1:160 dilution; Sigma) in PBS for 1 hr. The cells then were washed with PBS three times to remove unbound secondary antibody and were mounted with 70% glycerin. Fluorescence microscopy was performed using a Nikon Model 401 Fluorescence Microscope. Phase-contrast photomicrographs (FIGS. 15, A and C) and actin staining (FIGS. 15, B and D).

The morphological change observed in these transfected cells may be due, at least in part, to altered intigrin-cytoskeletal assemblies. To examine the possible effects on cytoskeleton, cells were treated with cytochalasin D, to inhibit actin polymerization, and then stained with anti-actin antibody (FIG. 15). Under these conditions, pcDNA3 transfected control cells maintained their original bipolar or triangular cell morphology and some actin filament structure. On the other hand, the transfected cells had a more rounded or cobblestone morphology. Upon cytochalasin D treatment, the cell body retracted towards the center of the cell with many focal adhesion plaques. No actin fibers were detected and actin staining was only observed at the center of cell body and at focal adhesion plaques.

Example 4
Decreased Tumorigenicity of α2,6-ST+ Glioma

As demonstrated above, transfection of the α2,6-ST gene into glioma cells caused a marked inhibition of glioma cell invasivity and a significant reduction in adhesivity to the extracellular matrix molecules, fibronectin and collagen. Furthermore, α3β1 integrin was found to contain α2,6-linked sialic acids, and tyrosine phosphorylation of p125$^{fak}$ was blocked in the transfectants despite increased expression of p125$^{fak}$ message. These data suggest that glycosyltransferase gene transfection may be a novel way to inhibit or retard glioma invasivity in vivo.

A. Tumorigenicity of non-transfected vs. transfected glioma cells

Figure 16:
FIG. 16. Tumorigenicity of parental U373MG cells compared to α2,6-Sialyltransferase clone J20.

To demonstrate that transfection of a sialyltransferase gene into a glioma cell would result in decreased tumorigenicity, untransfected U373 MG were implanted into a mouse host. Tumor cell growth was compared to that of the α2,6-ST-transfected U373 MG cells. As demonstrated in FIG. 16, implantation of the untransfected U373 MG cells resulted in significant tumor development; in contrast, the α2,6-ST-transfected U373 MG cells did not develop into tumors. This data indicates that expression of the α2,6-ST enzyme in glioma tumor cells inhibits the growth of these tumor cells in vivo.

In vivo tumorigenicity of human U373MG cells stably expressing high levels of transfected α2,3 sialyltransferase was evaluated by subcutaneous implantation into the flanks of nude mice. Three to ten million cells in a 50–100 μl volume were injected into a flank. Although these cells produced no measurable tumors on the flanks, it was noted that after an extended period of time (approximately 4 to 5 months), visible, palpable tumors appears elsewhere in some of the animals (2/10): one infiltrative spinal tumor and one within the renal capsule. Although no visible tumors could be observed in the other mice, all of the animals demonstrated a significant decline in general health status with time as compared to control mice of similar age. The average body weight of these animals declined to approximately half (12 g/26 g) over this extended time course. Significant spinal deformation and limb paralysis was also observed in most of the experimental animals. These observations, consistent with the in vitro experiments demonstrating direct correlation between α2,3 sialyltransferase expression and invasivity, provide additional evidence that modification of cell surface glycosylation may be an effective therapy for malignant gliomas.

B. Immuono-resistance of α2,6-ST expressing glioma cells

Since malignant gliomas are resistant to T-cell mediated lysis, increased terminal sialylation may be important in their ability to escape immune surveillance.

Example 5
Development of a Replication-deficient Adeno/α2,6-ST Virus

Figure 17:
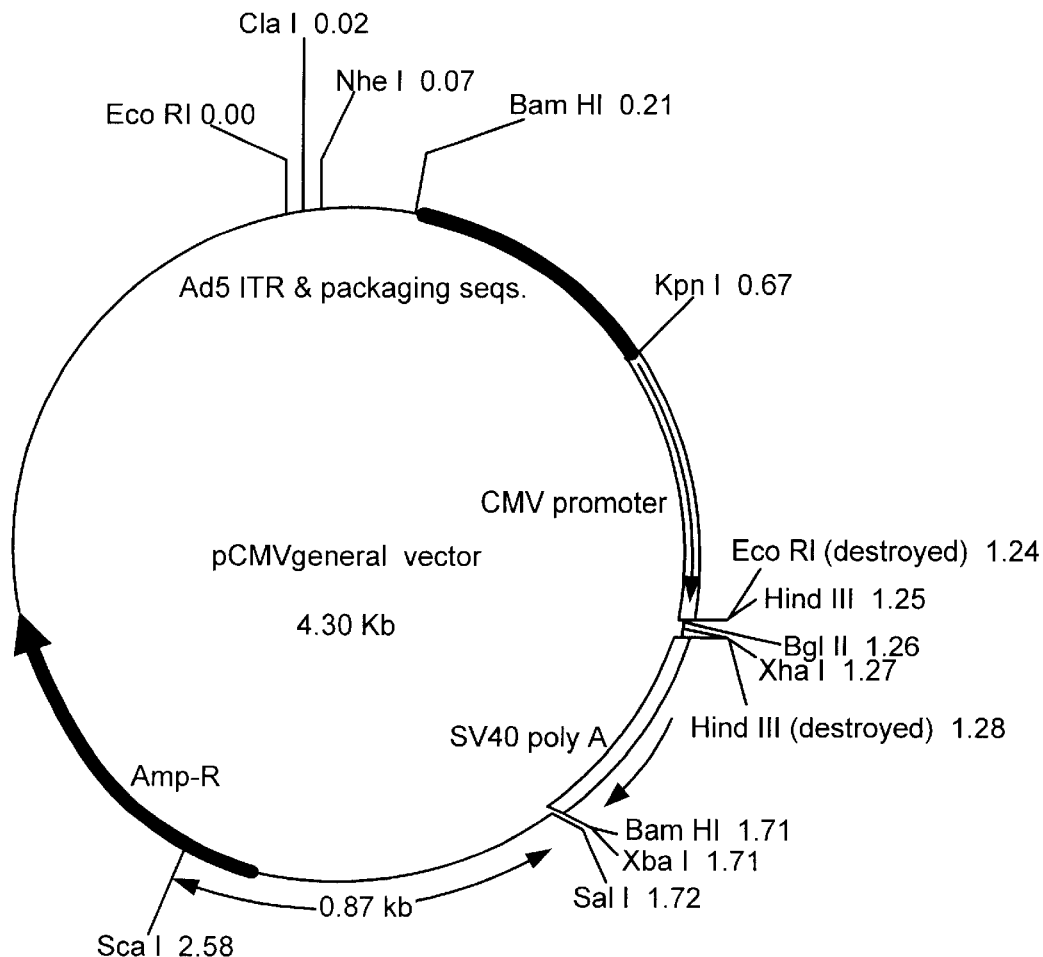
FIG. 17. Plasmid pCMV general vector.

Rat α2,6-ST cDNA was excised from the plasmid by Eco RI restriction digestion and ligated into the shuttle vector pCMVG (FIG. 17) at the Hind III site after blunt-ending with DNA polymerase (Klenow fragment). Orientation of the α2,6-ST insert was confirmed by Apa I and Xho I restriction digestion. 25–40 μg of the pCMV-G/α2,6-ST plasmid was then digested with Cla I and Xba I restriction enzyems and the 3.3 kb fragment, which contains the viral packaging sequence and α2,6-ST cDNA, was purified. 50 μg of wild type adenovirus DNA was also digested with Xba I to remove the 1.4 kb fragment containing the E1A sequence and the 35 kb adenovirus DNA fragment was purified. 4 μg of the 3.3 kb DNA from the shuttle vector and 41 μg of the 35 kb DNA fragment were then ligated with T4 DNA ligase at 12° C. for 24 hrs with the addition of the ligase every 3 hrs. The ligation mixture was then transfected into 293 cells with a cationic liposome system, DOTAP (Boehringer Mannheim, Indianapolis). Typically, 45 μg of α2,6-ST plasmid DNA was disolved in 450 μl of Hepes buffer (pH7.4) and was gently mixed with 900 μl of DOTAP solution (270 μl of DOTAP and 630 μl of Hepes buffer) for 15 min at room temperature. The mixture was then diluted with 20 ml of serum-free DMEM and added to 293 cells in a 150 mm tissue culture dish. After incubation in a 10% $CO_2$ incubator for 6 hrs, the transfection medium was replaced by normal growth medium (DMEM containing 10% FBS). The transfected 293 cells were maintained until a cytopathic effect (CPE) was observed (typically 7–10 days). The transfected cells were then harvested and the crude virus mixture was extracted from the cells by repeated freeze-thawing. The crude virus extract was again applied to new 293 cells to amplify the virus titer and incubated for 48 hrs until a CPE was observed. The 293 infected cells were harvested and the crude virus stock was stored in a 15% glycerol solution at –20° C. 200 μl of $10^5$–$10^8$-fold dilution virus stock was applied to a new batch of 293 cells (70–80% confluent) in a 60 mm culture dish and incubated for 1 hr. The culture dish was then aspirated and cells overlaid with 0.75% bacto-agar containing culture medium. After 8–10 days of incubation, each plaque was punched out by pipets and the virus was extracted from each plaque. Each virus clone was then reinfected into 293 fresh cells and incubated until a CPE was observed. This expansion step was repeated as needed to obtain sufficient quantities of each clone.

To determine whether the Adeno/α2,6-ST virus was successfully generated virus DNA was isolated and used for PCR analysis using the appropriate restriction digestion protocol. 30 pmol each of a sense primer corresponding to the 5' sequence of the rat α2,6-ST gene and an antisense primer corresponding to a 3' sequence of the rat α2,6-ST gene were utilized. The PCR amplification cycle consisted of denaturation at 94° C. for 40 seconds, annealing at 50° C. for 40 seconds and elongation at 71° C. for one minute. After 35 cycles of amplification, the product was analyzed on a 1% agarose gel. the presence of a band of the predicted size indicates that the Adeno/α2,6-ST gene is infected into the "293 cells" and produced the replication incompetent Adeno/α2,6-ST virus (the "Ad2,6" virus). The trnsfected "293 cells" comprising Ad2,6 virus can be further expanded for utilization in the present invention.

High-titer viral stock is then added to a plate containing 293 cells at 70–80% confluence in infection media (minimal essential medium and 2% fetal bovine serum). After a 90-minute incubation period, complete media is added to each plate and the cells incubated for 24 to 36 hours until a cytopathic effect is observed. The cells are then harvested and resuspended in five ml of supernatant. To release the virus, the cells are alternately frozen and thawed five times to develop a crude viral lysate. The crude viral lysate is then overlayed on a cesium chloride density gradient. Ultracetrifugation is performed at 25,000 rpm for 24 hours. The adenovirus is then collected from the gradient with a 21-guage needle. The virus is then dialyzed three times for four hours each into 10 mmol/L Tris, pH 7.4, 1 mmol $MgCl_2$, and 10% (vol/vol) glycerol. The virus is then recovered, and stored at –70° C.

Example 6
Utilization of the Adeno/α2,6-ST Virus in vtiro

Figure 18:
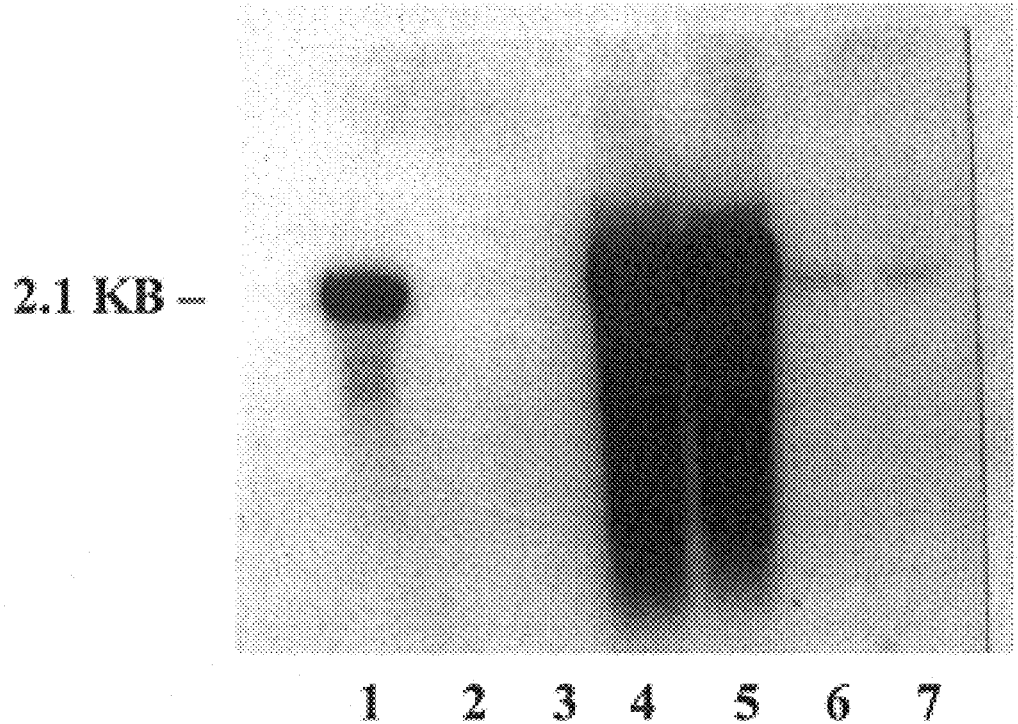
FIG. 18. Adenovirus-mediated gene expression of α2,6-sialyltransferase in U373MG glioma cells. Replication-deficient Adenovirus (200 pfu/cell) was used to express α2,6-sialyltansferase mRNA in the glioma cells. Lane 1: A stable transfectant of α2,6-sialyltransferase gene in U373MG glioma cells (clone J20) which express a 2.1 kb transcript; Lanes 2&3: Parental U373MG cells; Lanes 4&5: The Adeno/α2,6-ST virus-infected U373MG cells after 48 hrs of incubation; Lanes 6&7: U373MG cells tansiently transfected with the Adeno/α2,6-ST gene. Northern analysis was performed using a 1.6 kb rat α2,6-sialyltransferase cDNA. 20 µg per lane of total RNA was used. As shown in this figure, Adeno/α2,6-ST virus-mediated gene expression is much higher than stable transfection or transient transfection.

Replication-deficient Adenovirus (200 pfu/cell) was used to express α2,6-sialyltransferase mRNA in the glioma cells (FIG. 18). Northern blot analysis was performed using a 1.6 kb rat α2,6-sialyltransferase cDNA. 20 μg per lane of total RNA was used. As shown in this figure, Adeno/α2,6-ST virus-mediated gene expression is much higher than stable transfection or transient transfection.

Figure 19:
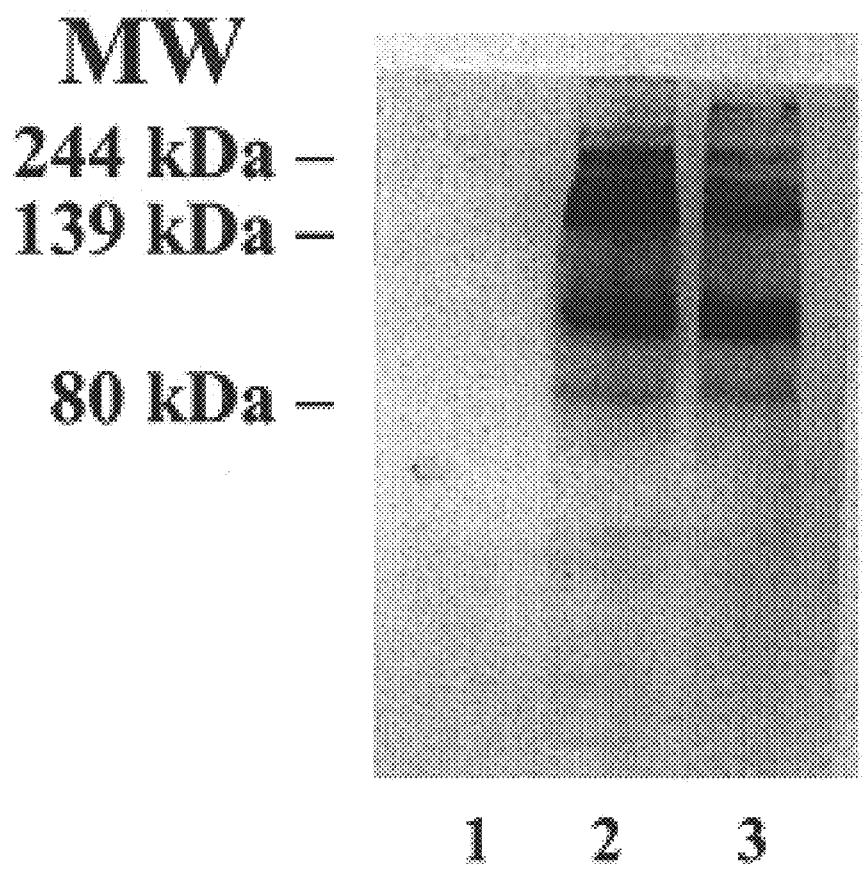
FIG. 19. Expression of α2,6-linked terminal sialic acid mediated by Adeno/α2,6-ST virus infection. Sambucus nigra agglutinin (SNA) lectin blotting was performed to detect terminal α2,6-linked sialic acids in U373MG cells infected by Adeno/α2,6-ST virus. 30 µg of each crude protein extract was separated by 10% SDS-polyacrylamide electrophoresis and the proteins were transfered to a PVDF membrane and biotinylated. SNA lectin (1 µg/ml) was used to detect terminal α2,6-linked sialic acids. Lane 1: Parental U373MG cells; Lane 2: α2,6ST stable transfectant (clone J11); Lane 3: The Adeno/α2,6-ST virus-infected U373MG cells after 48 hrs of incubation. Identical lectin staining patterns (e.g., protein α2,6-sialylation) was observed in the stable transfectant and Adeno/α2,6-ST virus-infected U373MG cells.
Figure 20:
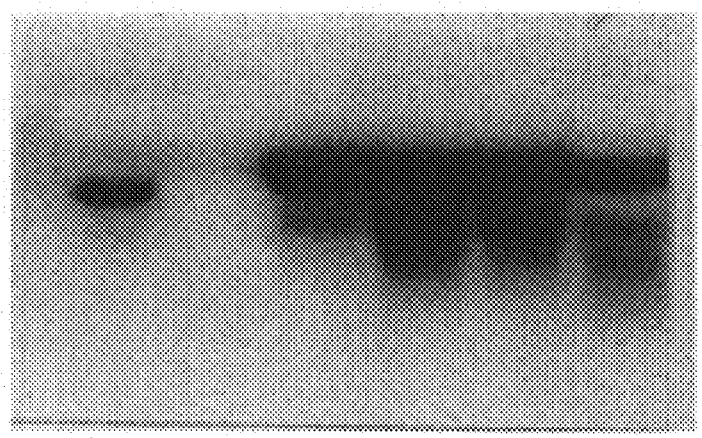
FIG. 20. Time course of Adenovirus-mediated gene expression of α2,6-sialyltransferase in U373MG glioma cells. Time course of the Adeno/α2,6-ST virus-mediated expression of α2,6-sialyltransferase mRNA in U373MG glioma cells. Lane 1: A stable transfectant of α2,6-sialyltransferase gene in U373MG glioma cell (clone J20) which express 2.1 kb transcript, lanes 2–6: Time course of α2,6-sialyltransferase mRNA expression in U373MG glioma cell infected by the virus (200 pfu/cell) at the time of 0, 24, 48, 72, and 120 hrs post-infection, respectively. The highest α2,6-sialyltransferase mRNA expression was observed at 48 hrs post-infection. Gene expression lasted at least 120 hrs in U373MG cells.

*Sambucus nigra* agglutinin (SNA) lectin blotting was performed to detect terminal α2,6-linked sialic acids in U373MG cells infected by Adeno/α2,6-ST virus (FIG. 19). 30 μg of each crude protein extract was separated by 10% SDS-polyacrylamide electrophoresis and the proteins we transferred to a PVDF membrane and biotinylated. SNA lectin (1 μg/ml) was used to detect terminal α2,6-linked sialic acids. The Adeno/α2,6-ST virus-infected U373MG cells after 48 hrs of incubation. Identical lectin staining patterns (e.g., protein α2,6-sialylation) was observed in the stable transfectant and Adeno/α2,6-ST virus-infected U373MG cells.

The time course of the Adeno/α2,6-ST virus-mediated expression of α2,6-sialyltransferase mRNA in U373MG glioma cells. The highest α2,6-sialyltransferase mRNA expression was observed at 48 hrs post-infection. Gene expression lasted at least 120 hrs in U373MG cells.

Example 7
Treatment of an Established Tumor in a Mammal Using a α2,6-ST Gene

The present invention may be utilized to treat a neurological disorder, exemplified herein using a rat brain tumor model. U373 MG cells are counted and resuspended in an appropriate physiologically acceptable buffer such as Hank's balanced salt solution (HBSS). The rat is anesthetized by administration of a composition comprising ketamine and placed into a stereotaxic frame. An incision is made in the scalp, and a burr bole of sufficient diameter is made using a dental drill. Using a 10 μl syringe fitted with a 26 gauge needle and connected to the manipulating arm of the stereotactic frame, U373 MG cells ($5 \times 10^5$ to $10^6$ cells in 7 μl HBSS) are injected in 0.2 μl increments over 5 minutes into the brain tissue at a depth of 4.5 mm from the dura. The needle is left in place for three minutes and then withdrawn over another three minutes. The burr hole is closed with bone wax and the scalp wound closed with clips. Tumors are then allowed to form within the brain until treatment as described below.

Stereotactic injection is utilized to administer a recombinant adenoviral vector ("Ad2,6") comprising a nucleic acid encoding α2,6-ST under the transcriptional control of the human CMV immediate-early enhancer/promoter into an established U373 MG tumor in a rat brain. Stereotactic injection of a composition comprising the recombinant adenoviral vector is performed. "Treated" animals are injected with a composition comprising $1.2 \times 10^9$ Ad-2,6 particles, and "untreated" animals are injected with a composition comprising $1.2 \times 10^9$ non-recombinant Ad viral particles (i.e., that from which Ad-2,6 was derived). The viral particles are suspended in 6 μl of 10 mM Tris-HCl, pH 7.4, 10% glycerol, and 1 mM $MgCl_2$ and injected at multiple sites within the tumor bed. Beginning at 5.5 mm below the dural surface, one μl is injected; the needle is then raised 0.5 mm and one μl is injected. A total of six injections are made. Virus injection takes place over five minutes and the needle is removed over five minutes. Carbon particles are placed over the shaft of the injection needle to mark the injection site and the wound is closed with clips. Following administration of the adenoviral particles to the tumors, the effectiveness of the treatment is determined by measurement of tumor growth in treated vs. untreated animals. It is demonstrated that treated animals exhibit less tumor growth than the untreated animals, thus indicating that expression of 2,6-ST in a brain tumor results in a decreased ability of a brain tumor to thrive.

Example 8
Method for Prevention of Brain Tumors Following Surgical Resection of Tumor The reagents and methodologies provided by the present invention are useful for prevention of neurological disorders, exemplified herein by prevention of tumor recurrence following surgical resection of a brain tumor. Following administration of general anesthesia, a craniotomy is performed on a patient having a glioblastoma brain tumor. The exact location of the brain tumor is determined prior to surgery using an MRI. As much as possible of the brain tumor is then surgically removed. Following removal of the tumor, a pharmaceutical composition comprising the Ad2,6 viral vector suspended in a liposomal formulation (DOTAP in saline) is applied to the area from which the tumor was removed. The amount of viral particle to be applied may vary but every attempt is made to apply the greatest number of viral particles in as small a volume as possible. The titer of the pharmaceutical composition is optimally $10^6$–$10^{12}$ viral particles/ml. The effectiveness of the treatment is measured by MRI scanning of the patient's brain at sufficiently timed intervals (optimally, once per week for one year) to determine that tumor cells have not begun to proliferate.

While a preferred form of the invention has been shown in the drawings and described, since variations in the preferred form will be apparent to those skilled in the art, the invention should not be construed as limited to the specific form shown and described, but instead is as set forth in the claims.

LITERATURE CITED

Kojima, N., N. Kurosawa, T. Nishi, N. Hanai, and S. Tsuji. Induction of cholinergic differentiation with neurite sprouting by de novo biosynthesis and expression of CD3 and b-series gangliosides in Neuro2a cells. J. Biol. Chem., 269: 0451–30456, 1994.

Demetriou, M., I. R. Nabi, M. Coppolino, S. Dedhar, and J. W. Dennis. Reduced contact-inhibition and sustratum adhesion in epithelial cells expressing GlcNActransferase V. J. Cell *Biol.,*130: 383–392, 1995.

Takano, R., F. Muchmore, and J. W. Dennis. Sialylation and malignant potential in tumor cell glycosylation mutants. Glycobiology, 4: 665–674, 1994.

Le Marer, N., V. Laudet, B. C. Svensson, H. Cazlaris, B. Van Hille, C. Lagrou, D. Stehelin, I. Montreuil A. Verbert, and P. Delannoy. The c-Ha-ras oncogene induces increased expression of β-galactoside α2,6-sialyltransferase in rat fibroblast (FR3T3) cells. Glycobiol., 2 : 49–56, 1992.

Le Marer, N. and D. Stehelin. High α2,6-sialylation of N-acetyllactosamine sequences in ras-transformed rat fibroblasts correlates with high invasive potential. Glycobiol., 5: 219–226, 1995.

Dall'Olio, F., M. Chiricolo, P. Lollini, and J. T. Lau. Human colon cancer cell lines permanently expressing α2,6-sialylated sugar chains by tmansfection with rat β-galactoside α2,6-sialyltransferase cDNA. Biochem. Biophys. Res. Commun., 211: 554–561, 1995.

Vertino-Bell, A., I. Ren, J. D. Black, and J. T. Lau. Developmental regulation of β-galactosidase α2,6-sialyltransferase in small intestine epithelium Dev. Biol., 165: 126–136, 1994.

Kitagawa, H. and J. C. Paulson. Differential expression of five sialyltransferase genes in human tissues. J. Biol. Chem., 269: 17872–17878, 1994.

Kaneko, Y., H. Yamamoto, D. Kersey, K. J. Colley, J. E. Leestma, and J. R. Moskal. The expression of Galβ1,4GlcNAc α2,6-sialyltransferase and α2,6-linked sialoglycoconjugates in human brain tumors. Acta Neuropath., 91: 284–292, 1996.

Yamamoto, H., Y. Kaneko, D. VanderMeulen, D. Kersey, E. Mkrdichian, L. Cerullo, J. Leestma, and J. R. Moskal. The expression of CMPNeuAc:Galβ1,4GlcNAc α2,6 sialyltransferase and glycoproteins bearing α2,6-linked sialic acids in human brain tumors. Glycoconjugate J. 12 : 848–856, 1995.

Kaneko, Y., H. Yamamoto, K. J. Colley, and J. R. Moskal. Expression of Galβ1,4GlcNAc α2,6-sialyltransferase and α2,6-linled sialoglycoconjugates in normal human and rat tissues. I. Histochem. Cytochem.,43: 945–954, 1995.

Paulus, W. and J. C. Tomm. Basement membrane invasion of glioma cells mediated by integrin receptors. J. Neurosurgery, 80: 515–519, 1994.

Ciancotti, F. C. and F. Mainiero. Integrin-mediated adhesion and signaling in tumorigenesis. Biochim. Biophys.Acta, 1198 : 47–64, 1994.

Juliano, R. L. The role of β1 integins in tumors. Sem. Cancer Biol., 4: 277–283, 1993.

Weinstein, I., E. U. Lee, K. McEntee, P. Lai, and J. C. Paulson. Primary structure of β-galactosidase α2,6-sialyltransferasc. J. Biol. Chem., 262 : 17735–17743, 1987.

Chomczynski, P. and N. Sacchi. Single-step method of RNA isolation by acid guanidinium thiocyanate-phenol-chloroform extraction Anal. Biochem., 1 62: 156–159, 1987.

Chirgwin, J. M., A. E. Przbyla, R. J. MacDonald, and W. J. Rutter. Isolation of biologically active ribonucleic acid from sources enriched in ribonuclease. Biochemistry, 18 : 5294–5299, 1979.

Paulson, J. C., L. Weinstein, and A. Schauser. Tissue-specific expression of sialyltransferases. J. Biol. Chem., 264:10931–10934, 1989.

Bresalier, R. S., R. W. Rockwell, R. Dahiya, Q-Y. Duh, and Y. S. Kim. Cell surface sialoprotein alterations in metastatic murine colon cancer cell lines selected in an animal model for colon cancer metastasis. Cancer Res., 50: 1299–1307, 1990.

Lee, B. U., J. Roth, and J. C. Paulson. Alteration of terminal glycosylation sequences on N-linked oligosaccharides of Chinese hamster ovary cells by expression of β-galactoside α2,6-sialyltransferase. J.Biol.Chem., 264: 13848–13855, 1989.

Cummings, R. D. and S. Komfeld. Characterization of the structural determinants required for the high affinity interaction of asparagine-linked oligosaccharides with immobilized *Phaseolus vulgaris* leukoagglutinating and erythroagglutinating lectins. J. Biol. Chem., 257: 11230–11234, 1982.

Hendrix, M. J. C., E. A. Seftor, R. E. B. Seftor, R. L. Misiorowski, P. Z. Saba, P. Sundareshan, and D. R. Welch Comparison of tumor cell invasion assays: human amnion versus reconstituted basement membrane barriers. Invasion Metas., 82 ::: 278–297, 1989.

Mosmann, T. Rapid colorimetric assay for cellular growth and survival: Application to proliferation and cytotoxicity assays. J. Immunol. Methods, 65: 55–63, 1983.

Ruoslahti, B., N. A. Noble, S. Kagami, and W. A. Border. Integrins. Kidney Internatl. Supp., 44 : S17–S22, 1994.

Richardson, A. and J. T. Parsons. Signal transduction through integrins: a central role for focal adhesion kinase? Bioessays, 17: 229–236, 1995.

Rosales, C., V. O'Brien, L. Komberg, and R. Juliano. Signal transduction by cell adhesion receptors. Biochem.Biophys. Acta, 1242 : 7–98, 1995.

Hynes, R. O. Integrins: versatility, modulation, and signaling in cell adhesion. Cell, 69:11–25, 1992.

Ruoslahti, B. Integrins. J. Clin. Invest., 87: 1–5, 1991.

Yamada, K. M. Functions of integrins in cell adhesion and migration. AIDS Res. Hum. Retroviruses, 8: 786–793, 1992.

Yamada, K. M. Functions of integrins in cell adhesion and migration. AIDS Res. Hum. Retroviruses, 8: 786–793, 1992.

Kawano, T., S. Takasaki, T. W. Tao, and A. Kobata. Altered glycosylation of β1 integrins associated with reduced adhesiveness to fibronectin and laminin. Internatl. J. Cancer, 53 : 91–96, 1993.

Zheng, M., H. Fang, and S. Hakomori. Functional role of N-glycosylation in α5β1 integrin receptor. De-N-glycosylation induces dissociation or altered association of α5 and β1 subunits and concomitant loss of fibronectin binding activity. J. Biol. Chem., 269 : 12325–12331, 1994.

Akiyama, S. K., S. S. Yamada, and K. M. Yamada Analysis of the role of glycosylation of the human fibronectin receptor. J. Biol. Chem., 264 : 18011–18018, 1989.

vonLampe, B., A. Stallmach, and E. O. Riecken. Altered glycosylation of integrin adhesion molecules in colorectal cancer cells and decreased adhesion to the extacellular matrix. Gut, 34: 829–836, 1993.

Chammas, R., S. S. Veiga, L. R. Travassos, and R. R. Brentani. Functionally distinct roles for glycosylation of alpha and beta integrin chains in cell-matrix interactions. Proc. Natl. Acad. Sci. of the U.S.A.,90 : 1795–1799, 1993.

Clark, E. A. and J. S. Brugge. Integrins and signal transduction pathways: the road taken. Science, 268 : 233–239, 1995.

Schuppan, D., and M. Ruhl. Matrix in signal transduction and growth factor modulation. Brazil. I. Med. Biol. Res., 27: 2125–2141, 1994.

Schwartz, M. A. and D. E. Ingber. Integrating with integrins. Mol. Biol. Cell, 5: 389–393, 1994.

Sankar, S., N. Mahooti-Brooks, C. Hu, and J. A. Madri. Modulation of cell spreading and migration by pp12sfak phosphorylation. Amer. J. Path., 147: 601–608, 1995.

Couchman, J. R., D. A. Rees, M. R. Green, and C. G. Smith. Fibronectin has a dual role in locomotion and anchorage of primary chick fibroblasts and can promote entry into the division cycle. I. Cell B., 93 : 402–410, 1982.

Rodriguez Fernandez, J. L., B. Geiger, D. Salomon, and A. Ben-Ze'ev. Overexpression of vinculin suppresses cell motility in BALB/c3T3 cells. Cell Mot. Cytoskel., 22 : 127–134, 1992.

Sata, T., J. Roth, C. Zuber, B. Stamm, and P. U. Heitz. Expression of 0:2,6-linked sialic acid residues in neoplastic but not in normal human colonic mucosa Amer. J. Path., 139: 1435–1448, 1991.

Bresalier, R. S., R. W. Rockwell, R. Dahiya, Q-Y. Duh, and Y. S. Kim. Cell surface sialoprotein alterations in melastatic murine colon cancer cell lines selected in an animal model for colon cancer metastasis. Cancer Res., 50: 1299–1307, 1990.

Dennis, J., C. Waller, R. Timpl, and V. Schimnacher. Surface sialic acid reduces attachment of metastatic tumour cells to collagen type IV and fibronectin. Nature, 300 : 274–276, 1982.

Kijima-Suda, I., Y. Miyamoto, S. Toyoshima, M. Itoh, and T. Osawa. Inhibition of experimental pulmonary metastasis of mouse colon adenocarcinoma 26 sublines by a sialic acid: nucleoside conjugate having sialyltransferase inhibiting activity. Cancer Res., 46: 858–862 1986.

DiMilla, P. A., Barbee, K., and Lauffenburger, D. A. Mathematical model for the effects of adhesion and mechanics on cell migration speed. Biophys. J, 60: 15–37, 1991.

Lauffenburger, D. A. A simple model for effects of receptor-mediated cell-substratum adhesion on cell migration. Chem. Eng. Sci., 44: 1903–1914, 1989.

DiMilla, P. A., Stone, J. A., Quinn, J. A., Albelda, S. M., and Lauffenburger, D. A. An optimal adhesiveness exists for human smooth muscle cell migration on type IV collagen and fibronectin. J. Cell. Biol., 122;: 729–737, 1993.

Albelda, S. M. Role of integrins and other cell adhesion molecules in tumor progression and metastasis. Lab. Invest. 68 : 4–17, 1993.

Wu, P., Hoying, J. B., Williams, S. K., Kozikowski, B. A., and Lauffenburger, D. A. Integrin-binding peptide in solution inhibits or enhances endothelial cell migration, predictably from cell adhesion. Annals Biomed. Eng., 22 : 142–152, 1994.

Keely, P. J., Fong, A. M., Zutter, M. M., and Santoro, S. A. Alteration of collagendependent adhesion, motility, and morphogenesis by the expression of antisense α2 integrin mRNA in mammary cells. J. of Cell Sci., 108 (Pt 2): 595–607, 1995.

Bastida, E., Almirall, L., Jamieson, G. A., and Ordinas, A. Cell surface sialylation of two human cell lines and its correlation with their platelet-activating activity. Cancer Res., 47 (1987) 1767–1770.

Bresalier, R. S., Rockwell, R. W., Dahiya, R., Duh, Q-Y., and Kim, Y. S. Cell surface sialoprotein alterations in metastatic murine colon cancer cell lines selected in an animal model for colon cancer metastasis. Cancer Res., 50 (1990) 1299–1307.

Broquet, P., Baubichon-Cortay, H., George, P., and Peschard, M. J. Effect of desipramine on a glycoprotein sialyltransferase activity in C6 cultured glioma cells. J. Neurochem., 54 (1990) 388–394.

Broquet, P., George, P., Geoffroy, J., Reboul, P., and Louisot, P. Study of 0-glycan sialylation in C6 cultured glioma cells: evidence for post-tanslational regulation of a beta-galactoside alpha 2,3 sialyltranferase activity by N-glycosylation. Biochem. Biophys. Res. Commun., 178 (1991)1437–1443.

Collard, J. G., Schijven, J. F., Bikker, A., LaRifiere, C., Bolscher, J. G. M., and Roos, E. Cell surface sialic acid and the invasive and metastatic potential of T-cell hybridomas. Cancer Res., 46 (1987) 3521–3527.

Dennis, I., Waller, C., Timpi, R., and Schirrmacher, V. Surface sialic acid reduces attachment of metastatic tumor cells to collagen type IV and fibronectin. Nature, 300 (1982) 274–276.

Gomati, R., Basu, S., Montorfano, C., and Berra, B. Glycosyltransferase activites in human meningiomas. Preliminary results. Cancer Biochem. Biophys., 15 (1995) 1–10.

Grimes, W. J. Sialic acid transferases and sialic acid levels in normal and transformed cells. Biochemistry, 12 (1973) 990–996.

Kaneko, Y., Yamamoto, H., Kersey, D., Colley, K., Leestma, J., and Moskal, J. Expression of Galβ1,4GlcNAc α2,6 sialyltransferase and α2,6-linked sialoglycoconjugates in human brain tumors. Acta Neuropath., 91(1996) 284–292.

Kepes, J. I. Review of the WHO's proposed new classification of brain tumors. Proceedings of the XIth International Congress of Neuropathology, Kyoto, Sep. 2–8, 1990. Japanese Society of Neuropathology, Kyoto, Japan.

Kitagawa, H., and Paulson, J. C. Differential expression of five sialyltransferase genes in human tissues. J. Biol. Chem., 269 (1994) 17872–17878.

Le Marer, N., and Stehelin, D. High alpha-2,6-sialylation of N-acetyllactosamine sequences in ras-transformed rat fibroblasts correlates with high invasive potential. Glycobiolgy, 5 (1995) 219–226.

Moskal, J. R., Gardner, D. A. and Basu, S. Changes in glycolipid glycosyltransferases and glutamate decarboxylase and their relationship to differentiation in neuroblastoma cells. Biochem. Biophys. Res. Corn m U n., 61 (1974) 751–758.

Nicholson, G. L. Cancer metastasis-organ colonization and the cell surface properties of malignant cells. Biochem. Biophys. Acta, 695 (1982) 113–176.

Passaniti, A. and Hart, G. W. Cell surface sialylation and tumor metastasis. I. Biol. Chem., 263 (1988) 7591–7603.

Reboul, P., Broquet, P., George, P., and Louisot, P. Effect of reeinoic acid on two glycosyltransferase activites in C6 cultured glioma cells. Int. J. Biochem., 22 (1990) 889–893.

Roth, J. Cellular sialoglycoproterms: a histochemical perspective. Histochem. J. 25 (1993) 687–710.

Rutka, J. T., Apodaca, C., Stem, R., and Rosenblum, M. The extracellular matrix of the central and peripheral nervous system: structure and function. J. Neurosurg., 69 (1988) 155–170.

Sata, T., Roth, J., Zuber, C., Stamm, B., and Heitz, P. U. Expression of α2,6-linked sialic acid residues in neoplastic but not in normal human colonic mucosa. Am. J. Pathol., 139 (1991) 1435–1448.

Schirrmacher, V., Altevogt, P., Fogel, M., Dennis, J., Waller, C. A., Barz, D., Schwartz, R. et al. Importance of cell surface carbohydrates in cancer cell adhesion, invasion, and metastasis. Invasion Metastasis, 2 (1982) 313–360.

Shen, A. L., Chou, M. D., Chi, C. W., and Lee, L. S. Alterations in serum sialyltransferase activities in patients with brain tumors. Surg. Neurol., 22 (1984) 509–514.

Stoykova, L. I. and Click, M. C. Purification of an alpha-2,8-sialyltranferase, a potential initiating enzyme for the biosynthesis of polysialic acid in human neuroblastoma cells. Biochem. Biophys. Res. Commun. 217 (1995) 777–783.

Varki, A. Biological roles of oligosaccharides: all of theories are correct. Glycobiology, 3 (1993) 97–130.

Wang, W-C., and Cummings, R. D. The immobilized leukoagglutinin from the seeds of Maackia amurensis binds with high affinity to complex-type Asn-linked oligosaccharides containing terminal sialic acid-linked α-2,3 to penultimate galactose residues. J. Biol. Chem., 263 (1988) 4576–4585.

Warran, L., Fuhrer, J. B., and Buck, C. A. Surface glycoproteins of normal and transformed cells: a difference determined by sialic acid and a growth-dependent sialyltransferase. Proc. Nati. Acad. Sci. USA, 69 (1972) 1838–1842.

Wen, D. X., Livingston, B. D., Medzihradszky, K. F., Keim, S., Burlingame, A. L., and Paulson, J. C. Primary structure of Galβ1,3(4)GlcNAc α2,3-sialyltransferase determined by mass spectrometry sequence analysis and molecular cloning. J. Biol. Chem., 267 (1992) 21011–21019.

Werkmeister, J. A., Pross, H. F., and Roder, J. C. Modulation of K562 cells with sodium butyrate. Association of impaired NK susceptibility with sialic acid and analysis of other parameters. Int. J. Cancer, 32 (1983) 71–78.

Yamamoto, H., Kaneko, Y., VanderMeulen, D., Kersey, D., Mkrdichian, E., Cerullo, L., Leestina, I., and Moskal, I. R.

The expression of CMP-NeuAc:Galβ1,4GlcNAc α2,6 sialyltransferase and glycoprotems bearing α2,6-linked sialic acids in human brain tumors. *Glycoconjugate J.,* 12 (1995) 848–856.

Yong, W. V., Tejada-Berges T., Goodyer, C. C., Antel, J. P., and Yong, F. P. Differential proliferative responses of human and mouse astrocytes to gamma-interferon, *Glia,* 6 (1992) 269–280.

Zagzag, D., Friedlander, D. R., Miller, D. C., Dosik, I., Cangiarella, J., Kostianovsky, M., Coheo, H., Grumet, M., and Greco, M. A. Tenascin expression in aocytomas correlates with angiogenesis. *Cancer Res.,* 55 (1995) 907–914.

Patel et al., 1994. *Human Gene Therapy* 5, p. 577–584.

*Human Gene Therapy* April 1994, Vol. 5, p. 543–563.

Mulligan, R. C. 1993. The basic science of gene therapy. *Science* 260: 926–932.).

Miller, A. D., and G. J. Rosman. 1989. Improved retroviral vectors for gene therapy and expression. *Biotechniques* 7: 980–990.

Stratford-Perricaudet, L., and M. Perricaudet. 1991. Gene transfer into animals: the promise of adenovirus. p. 51–61, *In: Human Gene Transfer,* Eds, O. Cohen-Haguenauer and M. Boiron, Editions John Libbey Eurotext, France.)

Levrero, M., et al. 1991. Defective and nondefective adenovirus vectors for expressing foreign genes in vitro and in vivo. *Gene* 101: 195–202.

Graham, F. L., and L. Prevec (1992) Adenovirus-based expression vectors and recombinant vaccines. In Vaccines: New Approaches to Immunological Problems, (Ellis, R. V. Ed.), pp. 363–390. Butterworth-heinemann, Boston.

Stratford-Perricaudet, et al. 1992. Widespread long-term gene transfer to mouse skeletal muscles and heart. *J. Clin. Invest.* 90, 626–630.

Rich, et al. 1993. Development and analysis of recombinant adenovinises for gene therapy of cystic fibrosis. *Human Gene Ther.* 4, 461–476.

Crystal, et al. 1994. *Nature Genetics* 8, 42–51.

Rosenfeld, et al. 1992. In vivo transfer of the human cystic fibrosis transmembrane conductance regulator gene to the airway epithelium. *Cell* 68, 143–155.

Quantin, B., et al. 1992. Adenovirus as an expression vector in muscle cells in vivo. *Proc. Natl. Acad. Sci. USA* 89, 2581–2584.

Herz, J. and R. D. Gerard. 1993. Adenovirus-mediated transfer of low density lipoprotein receptor gene acutely accelerates cholesterol clearance in normal mice. *Proc. Natl. Acad. Sci. USA* 90, 2812–2816.

Le Gal La Salle, et al. 1993. An adenovirus vector for gene transfer into neurons and glia in the brain. *Science* 259, 988–990.)

Hermonat, P. L., and N. Muzyczka. 1984. Use of adeno-associated virus as a mammalian DNA cloning vector: transduction of neomycin resistance into mammalian tissue culture cells. *Proc. Natl. Acad. Sci. USA* 81: 6466–6470.

Geller, A. I., and H. J. Federoff. 1991. The use of HSV-1 vectors to introduce heterologous genes into neurons: implications for gene therapy. *In: Human Gene Transfer,* Eds, O. Cohen-Haguenauer and M. Boiron, pp. 63–73, Editions John Libbey Eurotext, France.

Glorioso, et al. 1995. Herpes simplex virus as a gene-delivey vectors for the central nervous system. *In: Viral Vectors-Gene therapy and neuroscience application,* Eds, M. G. Kaplitt and A. D. Loewy, pp. 1–23. Academic Press, New York.

Smith, G. L., and B. Moss. 1983. Infectious poxvirus vectors have capacity for at least 25,000 base pairs of foreign DNA. *Gene* 25: 21–28; Moss, B. 1992. Poxviruses as eukaryotic expression vectors. *Semin. Virol.* 3: 277–283.

Oldfield, et al. 1993. Gene Therapy for the Treatment of Brain Tumors Using Intra-Tumoral Transduction with the Thymidine Kinase Gene and Intravenous Ganciclovir, *Human Gene Therapy* 4:39–69.

Doll, et al. 1996. Comparison of promoter strengths on gene delivery into mammalian brain cells using AAV vectors. *Gene Therapy* 3: 437–447.

Badie, et al. 1994. Stereotactic Delivery of a Recombinant Adenovirus into a C6 Glioma Cell Line in a Rat Brain Tumor Model. *Neurosurgery* 35: 910.

Perez-Cruet, et al. 1994. Adenovirus-Mediated Gene Therapy of Experimental Gliomas. *J. Neur. Res.* 39: 506.

Chen, et al. 1994. Gene therapy for brain tumors: Regression of experimental gliomas by adenovirus-mediated gene transfer in vivo. *Proc. Natl. Acad. Sci. USA* 91: 3054.

Oldfield, et al. 1993. Gene Therapy for Treatment of Brain Tumors Using Intra-Tumoral Transduction with the Thymidine Kinase Gene and Intravenous Ganciclovir. *Human Gene Therapy* 4:39–69.

Okada, et al. 1996. Gene therapy against an experimental glioma using adeno-associated virus vectors. *Gene Therapy* 3: 957–964.

Culver, et al. 1994. Gene Therapy for the Treatment of Malignant Brain Tumors with in vivo Tumor Transduction with the Herpes Simplex Thymidine Kinase Gene/Ganciclovir System, *Human Gene Therapy* 5: 343–379.

Stratford-Perricaudet, et al. 1990. *Human Gene Therapy* 1:241–256.

Moskal, et al. 1987. Effect of Retinoic Acid and Phorbol-12-myristate-13-acetate on glycosyltransferase Activities in Normal and Transformed Cells. *Cancer Res.* 47:787–790.

Hakomori, S-i. 1981. Glycosphingolipids in cellular interaction, differentiation, and oncogenesis. *Ann. Rev. Biochem.* 50:733–764.

Rademacher, et al. 1988. Glycobiology. *Ann. Rev. Biochem.* 57:785–838.

We claim:

1. A method of detecting the tumorigenicity or malignancy of a brain cell, comprising measuring the expression of glycosyltransferase within said cell, whereby the tumorigenicity or malignancy of the brain cell is detected.

2. A method of claim 1 wherein said glycosyltransferase is selected from the group consisting of α2,3-ST glycosyltransferase, α2,6-ST glycosyltransferase, HexB glycosyltransferase, Fuco glycosyltransferase, GnTIII glycosyltransferase, GnTI glycosyltransferase, SLex-ST glycosyltransferase and GnTV glycosyltransferase.

3. A method of claim 1 wherein said detection is accomplished by detection of nucleic acid sequences specific for glycosyltransferase.

* * * * *